(12) United States Patent
Mattsson et al.

(10) Patent No.: US 8,945,207 B2
(45) Date of Patent: Feb. 3, 2015

(54) REMOVABLE STENT AND METHOD OF PRODUCTION

(75) Inventors: Erney Mattsson, Västra Frölunda (SE); Torbjörn Lundh, Billdal (SE)

(73) Assignee: Graftcraft I Göteborg AB, Billdal (SE)

( * ) Notice: Subject to any disclaimer, the term of this patent is extended or adjusted under 35 U.S.C. 154(b) by 233 days.

(21) Appl. No.: 12/926,952

(22) Filed: Dec. 20, 2010

(65) Prior Publication Data
US 2012/0158122 A1    Jun. 21, 2012

(51) Int. Cl.
*A61F 2/90*    (2013.01)
*B21F 45/00*    (2006.01)
*A61F 2/856*    (2013.01)
*A61F 2/95*    (2013.01)

(52) U.S. Cl.
CPC ............. *B21F 45/008* (2013.01); *A61F 2/856* (2013.01); *A61F 2/90* (2013.01); *A61F 2002/9528* (2013.01)
USPC .......................................... 623/1.51; 623/1.15

(58) Field of Classification Search
CPC ..................... A61F 2/90; A61F 2/70
USPC ............ 623/1.33, 1.39, 1.15, 1.22, 1.5–1.53; 66/169 R, 170
See application file for complete search history.

(56) References Cited

U.S. PATENT DOCUMENTS

| | | | |
|---|---|---|---|
| 5,383,928 A | | 1/1995 | Scott et al. |
| 5,514,176 A | * | 5/1996 | Bosley, Jr. ................... 623/1.15 |
| 5,733,327 A | * | 3/1998 | Igaki et al. .................... 623/1.5 |
| 6,981,987 B2 | | 1/2006 | Huxel et al. |
| 7,252,680 B2 | | 8/2007 | Freitag |
| 2003/0185752 A1 | * | 10/2003 | Nathan et al. ................ 424/1.11 |
| 2005/0080480 A1 | | 4/2005 | Bolea et al. |
| 2005/0256075 A1 | | 11/2005 | Alitalo et al. |
| 2006/0276887 A1 | | 12/2006 | Brady et al. |
| 2007/0055364 A1 | | 3/2007 | Hossainy et al. |
| 2008/0071287 A1 | * | 3/2008 | Goto ............................. 606/108 |
| 2008/0138375 A1 | | 6/2008 | Yan et al. |
| 2008/0146489 A1 | | 6/2008 | Pacetti et al. |

FOREIGN PATENT DOCUMENTS

| | | |
|---|---|---|
| WO | WO-93/15787 A1 | 8/1993 |
| WO | WO-99/51299 A2 | 10/1999 |
| WO | WO-2005/058201 A1 | 6/2005 |

* cited by examiner

*Primary Examiner* — Christopher D Prone
(74) *Attorney, Agent, or Firm* — Harness, Dickey & Pierce, PLC

(57) ABSTRACT

A method and apparatus for a removable porous stent to be placed in tubular structures that is unsuitable for permanent stents. The walls of the stent are freely permeable to allow the blood flow. The stent can be used as a carrier of chemotherapy or radiation to be placed in tubular structures for local treatment of cancer. The stent is formed by at least one continuous thread arranged in interconnected loops and having a reversible bind-off at one end of the tubular body, mechanically securing each loop at said end of the tubular body apart from a single releasable loop. This loop is preferably extended beyond the tubular structure of the stent enabling an initiation of the removal at a distance from the treatment site.

24 Claims, 21 Drawing Sheets

REMOVABLE STENT AND METHOD OF PRODUCTION

TECHNICAL FIELD OF THE INVENTION

The present invention relates to a removable stent which is useable to treat dissections, and which can give temporary and local treatment by means of active substances or irradiation. The invention is also related to a method for producing such a stent.

BACKGROUND

Aortic dissection has the primary pathology of an intimal tear that penetrates the aortic media, as is illustrated in FIG. 2. This entry tear often occurs at sites of greatest wall tension, usually within a few centimeters of the aortic valve on the right lateral wall of the ascending aorta. This is commonly referred to as type A dissection. Blood at high pressure then splits or dissects the aortic media to form a false channel or lumen that runs alongside the true lumen, as is illustrated in FIG. 3. Aortic dissection is one of the most common and lethal illness conditions involving the aorta. Rapid diagnosis as well as an appropriate therapy is essential for survival of the patients. Acute type A dissection, which involves the ascending aorta, normally has a mortality of 1% to 2% per hour during the first 48 hours after initiation. Further, it can quickly extend towards the heart and cause death by cardiac tamponade, blockage of coronary arteries or progress more distally to occlude aortic arch vessels.

Consequently, without surgical therapy, acute type A aortic dissection is nearly invariably lethal with an expected 90-day mortality of 70% to 90%. With modern medical management, the survival rates are greater, but the mortality rate is still above 50%. Surgery includes extra corporal circulation with cerebral perfusion and implantation of a composite graft in the ascending aorta with or without re-implantation of coronary arteries and the aortic valve.

It has been shown that the risk of mortality from surgery for acute type A aortic dissection is high with increasing age. It is published figures of 45% for patients 80 to 84 years of age and 50% for those 85 years or older. As a consequence many patients are not treated with surgery, especially in the presence of high age and/or co-morbidities.

It is obvious that a less traumatic but still invasive alternative would be of importance for many cases. Endovascular treatment is often not possible because of the anatomical restrictions of securing a traditional stent graft within the ascending aorta. Furthermore, the dissection usually involves the aortic arch from which the arteries to the brain take off. Permanent coverage of this area carries continuous lethal danger. The lethal danger consists of the risk of clot formation on the stent material with the release of emboli to the brain. Furthermore, clot formation at numerous locations on a stent placed across aortic arch vessels might reduce the blood supply to the brain. Both risks will increase with increased time of presence of the stent, making permanent stents non-suitable for this type of treatment. The alternative of having a permanent stent combined with lifelong and aggressive anticoagulation carries high risks of bleeding complications. Cerebral hemorrhage with lethal outcome is a well-known side effect already with normal use of anti-coagulation in a lifelong perspective.

Even if the mortality rate is highest with acute type A dissections, also type B dissections may need interventions. The type B dissection is defined to have its entry to the false lumen distal to the left subclavian artery. It is usually treated conservatively but if indications such as intractable pain, a rapidly expanding aortic diameter, development of periaortic or mediastinal hematoma as signs of imminent aortic rupture are present, an intervention is often required. Often in these cases the type B dissection involves important side branches of the aorta. Sometimes the dissection extends into such side branches, which may then need a treatment of its own.

A dissection occurs in the media of the aortic wall. It is well-known that injury to this vessel wall layer induces an inflammatory response with neutrophil infiltration, fibrin formation, and smooth muscle cell proliferation. It stimulates a wound-healing mechanism. Spontaneous healing of aortic dissection is however very rare. Probably, because a flow of blood keeps the separated membrane apart from its original position. The placement of a permanent stent (in type B dissections) to approach the separated membrane to the media is known to facilitate healing of the dissection and sometimes of the entire aorta, including abdominal segments. The reason why permanent stents can be used in certain cases in dissections type B is that the extension of the dissection sometimes only includes the descending thoracic aorta, which does not have any crucial side branches. As soon as the visceral arteries are included or if a retrograde dissection occurs into the aortic arch, permanent stents are less suitable.

It is obvious that a temporary attachment of the separated membrane to the media during the healing process of the dissection would be an alternative for type A dissections and also for type B dissections with side branch involvement or for isolated important single branches. Temporary attachment would be preferred, because permanent coverage of the aortic arch and important side-branches carry too high risk. Such a suggested temporary approach might need simultaneous and aggressive anticoagulation therapy.

There is therefore a need for a removable stent that can be used for such treatments.

Another medical area of interest is temporary and local application of very powerful drugs or irradiation. As examples: it has been shown in clinical studies in head and neck cancer that the combination of cisplatin/epinephrine placed locally in an injectable gel may reduce the size of solid tumors, improve quality of life, and produce fewer traditional chemotherapy-related side effects than intravenous chemotherapy. Intralymph nodal injection or intraperitoneal administration of mitomycin C carried by small activated carbon particles seems to improve the survival rates and might be able to treat peritoneal metastases in gastric cancer. These treatments lack the possibility to regulate the timeframe, which of course influences, the dosages applied. Internal radiation for uterine cancer is one example of combined local application and regulated time for the treatment. In this treatment tiny tubes containing a radioactive substance are inserted through the vagina and left in place for a planned time period. No treatment is yet available for cancer in the gastro-intestinal tract including the esophagus or in the hepatico-pancreatico-biliar system with the characteristics of being local and where the time for treatment is under control. The same is true for parenchymal cancers such as pulmonary, hepatic and brain cancer. There are a number of oncological substances and potentially specific irradiation agents, which have shown partial effect against cancer. The use of these and similar factors is limited by side-effects when delivered systemically. The dosage that reaches the target area will thereby be reduced and so will the effect.

The use of stents in the treatment of e.g. arterial stenosis is well known in the art. The majority of stents used today are for permanent use. However, stents for temporary use are also described in the prior art. A temporary stent can either be removable or biodegradable so that it is degraded after a certain amount of time. Biodegradable stents, such as e.g. disclosed in WO9315787, US2007055364 and 6981987, have the advantage that they do not require an invasive removal procedure for non-permanent use. However, when using biodegradable stents it is not possible to control the treatment time in detail since the degradation of the stent is a slow chemical process. This has hindered the use of biodegradable stents for the treatment of e.g. aortic dissection where a short duration of treatment is needed to reduce the risk of embolism and to keep the duration of aggressive anticoagulation therapy at a minimum for safety reasons. The time for treatment if these stents carry either chemotherapy or irradiation cannot be precisely controlled. Polymeric biodegradable stents have demonstrated other limitations. Their mechanical strength is lower than e.g. metallic stents. The polymer alone has a limited mechanical performance and a recoil rate of approximately 20%, which requires thick struts that impede their profile and delivery capabilities. Further, they are associated with a significant degree of local inflammation. This reaction combined with the slow bioabsorption rate may result in restenosis. Also, these stents are radiolucent, which may impair accurate positioning and makes it impossible to control the position after delivery. Furthermore, it is difficult to deploy the stent smoothly and precisely without fluoroscopic visualization. The possibility to control the position is especially important if a stent carries potent treatment modalities.

Removable stents have the advantage that they can be removed at any time, either when the treatment is finalized or if the treatment needs to be terminated or relocated for any other reason. Unfortunately, the removable stents in the art all require an invasive removal procedure, using e.g. an endoscope, to contact the stent at the treatment site and then remove the stent from the treatment site. This removal procedure is associated with risk, especially around the treatment site where the tissue is likely to be extra sensitive for this type of manipulation because of the treated condition. This is of great importance in e.g. aortic dissections where the vascular wall just has undergone a reparative process that could risk being reversed by this type of manipulation. Also advanced cancer has bleeding tendencies and consists of fragile tissue, which makes it preferred to avoid any local manipulation. There is at present no available stent which enables removal in a non-invasive or minimally invasive manner.

Some examples of previously known removable stents will now be discussed briefly.

In US2008071287 a stent recovery apparatus that recovers a stent from a body cavity, e.g. the esophagus, is described. The device is inserted from outside the body into the body cavity where it catches one end of the stent before the removal can be initiated. When the proximal end of the stent is subjected to a pulling force the loops unwind and the stent can be removed in the form of a wire. The described stent and stent recovery apparatus are not suitable for the treatment of aortic dissections for several reasons. Firstly, a blood vessel such as the aorta is not a body cavity. Secondly, and more importantly, the stent does not have a high enough porosity to permit blood flow to important blood vessels from the aorta through the sides of the stent, an essential function if a stent is to be used in aortic dissections type A; the sparsity is also limited which also is a hindrance to a good blow flow through the surface into a side branch artery. Furthermore, the invasive removal procedure described in the application would risk the reversal of e.g. the healed aortic dissection since the inside of the blood vessel is very fragile at the treatment site or induce bleedings in well circulated cancer tissue alternatively perforations through the cancer tissue. Further, the stents disclosed in US2008071287 are very fragile, and there is a severe risk of uncontrolled disintegration at any location throughout its length during use.

U.S. Pat. No. 5,514,176 and WO 2005/058201 describe removable stents made as coils with adjacent loops packed tightly together. For removal of the stent, a surgical instrument, e.g. a forceps, is introduced from outside the body and contacts the proximal end of the stent, for detachment of adjacent loops from one another. These stents are substantially imperforate and virtually no blood can pass through the sides of the stent. This very limited permissiveness of blood flow through the sides of the stent makes the stent unsuitable for treatment of aortic dissections. In addition to the need for an invasive removal procedure, the relatively rigid and wide strand resulting from the detachment procedure is not particularly suitable for convenient removal. Further, these stents uses wires attached to an implant, making the stents rather costly and difficult to produce. Further, this increases the risk of separation between the wire and the implant, which would complicate the removal of the implant.

Another type of removable stents uses one or more wires wrapped around the implant, and useable to compress the implant, thereby reducing its diameter, for removal. Such stents are e.g. disclosed in U.S. Pat. No. 7,252,680, US2006276887 and US2005080480. However, with this type of removable stents, it is not possible to remove the implant without using an invasive removal procedure such as a new endoscopic procedure. Also, the diameter of the stent is still relatively large, even in the compressed state. Further, the stents of this type are also relatively complicated and costly to produce, and there is also a risk of separation between the collapsing elements and the implant, which would complicate the removal of the implant.

Stents delivering drugs, so called drug-eluting stents, are also known in the art and have been used since 2003, see e.g. U.S. Pat. No. 5,383,928, US2005256075, US2008138375 and US2008146489. Initially, drug eluting stents contained cytostatic compounds, that is, compounds that curtailed the proliferation of cells that resulted in restenosis. These stents all have the drawback of not being able to remove, which makes it impossible to regulate the time for treatment, including disables the possibility to interrupt the treatment in the case of side-effects.

In WO9951299 a stent for treatment of e.g. cancer and restenosis is described. In one embodiment, a composition having a radioactivable isotope incorporated into a matrix material is formed into a medical device, e.g. a stent. However, the stent is not constructed so that it can be removed, instead a low dose of a radioactive isotope with a short half-life is used to limit the duration of the treatment. Further, there is no possibility of controlling both the treatment site and the duration of the treatment.

There is therefore still a need for an improved removable stent.

SUMMARY OF THE INVENTION

There is therefore an object of the present invention to provide a removable stent and a method of producing such a stent that at least partly overcome the above-discussed problems of the prior art.

This object is achieved by means of a removable stent and a method of production according to the enclosed claims.

According to a first aspect of the invention there is provided a removable stent comprising a porous tubular body formed by at least one continuous thread arranged in interconnected loops and having a reversible bind-off at one end of the tubular body, mechanically securing each loop at said end of the tubular body apart from a single releasable loop.

Even though bind-off is usually used in connection with knitting, the concept of a reversible bind-off in the context of the present invention should be construed in a more general sense, indicating securing of each loop at the end of the tubular body apart from a single releasable loop. Accordingly, a reversible bind-off may also be formed when using other techniques than knitting for forming a tubular body by interconnected loops, such as when using crochet.

The reversible bind-off includes a loop which is not secured, but left open. By releasing this non-secured loop, the stent disintegrates. The presence of the reversible bind-off secures the structure of the stent while in use, but leaves the possibility to have a controlled disintegration at the time of choice. Thus with the reversible bind-off the structure is secured as in the more common traditional bind-off used in e.g. knitting, but the reversible bind-off includes the possibility to rip up the material, which is not possible with a traditional bind-off.

Due to the provision of the reversible bind-off, a mechanically stable tubular body is achieved, which retains it structure during use, and which is still very easy to remove, by releasing the reversible bind-off. During removal the stent is removable as a single thread. Hence, the removable stent of the present invention can be removed by a non-invasive or minimally invasive procedure where no additional external objects are required in close contact with the treatment site. This makes it possible to remove the stent without any extra instruments or new interventions. Hereby, no mechanical manipulation in the fragile treated area is necessary for the removal of the stent.

Further, the porosity of the tubular body of the stent permits blood flow to important blood vessels from the aorta through the sides of the stent.

These characteristics make it possible to use the present stent in several vascular positions that previously have not been possible.

Further, the stent according to the present invention is relatively easy to produce, making it very cost-efficient.

The removable stent may e.g. be used for treatment of a dissection, wherein the tubular body is provided with a radial strength enough to reattach the separated membrane to its original location along the vessel wall. Since the tubular wall is porous, making the stent walls permeable to blood, and preferably porous enough to allow free flow of blood through its structure, it may be arranged over branching off blood vessels, and still enable adequate blood supply to these vessels. The removability of the stent makes it easy to remove the stent, e.g. by pulling an extending part of the continuous thread, after the healing of the dissection.

Since the stent can be placed in locations where permanent stent treatment of today is not possible, it is, as an illustrating example, an alternative to big thoracic operations such as in the case of aortic dissection type A wherein control of position of said stent can be achieved by external x-ray.

The tubular body is preferably formed by a single continuous thread. Further, the stent is preferably essentially entirely formed by the at least one continuous thread. Hereby, there is no risk of unfolding between various parts, and the removal of the stent is further facilitated.

Preferably, the removable stent is further expandable from a contracted insertion state to an expanded use state. Hereby, the stent may be contracted or compressed for easy insertion, and can then be expanded to its expanded state at the intended site of use.

The at least one continuous thread preferably extends with a loose end from said single releasable loop, thereby enabling release of said reversible bind-off by pulling said loose end, and unraveling of the interconnected loops by further pulling of the loose end. Hence, the loose end may extend to a position distant from the tubular body, and may even extend to a position outside the patient's body, which further facilitates the removal. For example, the part of the loose end being farthest from the tubular body may be connected to the skin surface of the patient. Preferably, the loose end has a length extension being larger than the axial length of the tubular body, and preferably being larger than two times the axial length of the tubular body.

The loops of the at least one continuous thread are preferably interconnected by means of knitting. A knitted tubular body is very stable, provides porosity and is easy to unravel when used in combination with the reversible bind-off. The reversible bind-off will have minor variations depending on the plain stitch used for the tubular body. The knitting technique for the reversible bind-off will however preferably always involve knitting each loop before passing it over the next loop and a final loop which is not secured, but left open.

However, other ways of forming a tubular body by means of interconnected loops of one or several threads are also feasible. For example, it would be possible to form the tubular body by crochet. In this case, the reversible bind-off would be formed automatically by not securing the last loop, since, as a difference from knitting, only one loop is active at a time when using crochet.

The end of the tubular body having the reversible bind-off preferably comprises a wale in which all loops are mechanically secured by the reversible bind-off, and wherein at least one additional mechanically secured loop is arranged between the wale and the single releasable loop. Hereby, a very stable end is formed, which is at the same time easy to unravel.

The end of the tubular body being opposite to the end having the reversible bind-off preferably comprises a mechanically secured cast-on, in order to further increase the stability of the tubular body. This is equal to that the tubular body only can be unraveled from the end with the reversible bind-off and when doing so the final pulling will also turn the opposite end previously mechanically secured by a cast-on into a single thread.

The at least one continuous thread preferably comprises a material having a shape memory, and preferably at least one of a memory alloy, such as nitinol, and a memory polymer. Additionally or alternatively, the at least one continuous thread may comprise a material not having a shape memory, and preferably at least one of stainless steel, carbon, and plastic material.

The porosity of the wall of the tubular part is sufficient to allow blood to pass through the wall. The quality of the stent to let flow go through the sides may be defined in terms of a quantified degree of porosity or sparsity.

The degree of porosity may be defined as the ratio between the area of the pores of a given patch of the stent and the area of the patch itself. One way to measure this is to estimate the number of white pixel in the whole picture and divide it with the total number of pixels.

Sparsity may be seen as the amount of open area in the stent wall. Sparsity can be seen as a measure of the relation between the inflow area into the stent and the undisturbed outflow area through the stent-wall. High values of sparsity assure a good blood flow without too much of interfering threads that can assembly small particles and release them in bigger lumps, or cause a turbulent flow around those thin obstacles. Sparsity may be defined as the ratio of the diameter of a maximal circle in a typical open patch in the stent over the diameter of the stent. This maximal circle diameter of a typical open patch is the mean taken over a number of randomly choosen such patches. See FIG. 8 where the mean diameter (measured in number of pixels) of the patches containing a circle, is 110 pixels. The diameter of the whole stent is around 733 pixels, implying a sparsity of approximately 110/733=0.15.

Preferably, the porosity of the tubular body of the stent is between 0.73 and 1. More preferably, the porosity is between 0.75 and 0.99. Most preferably, the porosity is between 0.8 and 0.98. The sparsity of the tubular part of the stent is preferably in the range of 0.05 to 0.6. More preferably, the sparsity is in the range 0.07 to 0.5. Most preferably, the sparsity is in the range 0.10 to 0.4.

The removable stent may further comprise a bioactive agent, such as a chemotherapy agent. Alternatively or additionally, the removable stent may comprise a radioactive agent. The bioactive agent and/or the radioactive agent is preferably arranged as a coating or as an integral part of at least a section of the one or several continuous threads.

Hereby, the removable stent may be used for local treatment of diseases such as cancer in the gastrointestinal tract or any location which can be reached through a tubular system. Generalized treatments carry the disadvantages by limitation of dosage because of side-effects, which will affect the concentration at the target area. The removable stent described in this invention is a suitable carrier for bioactive and/or radioactive agents, either by carrying the modalities as coatings or as an integrated part of the material. Due to the easy removability of the stent, the treatment will be local and the time for treatment can be precisely controlled. Further, precise positioning of the stent can be achieved by e.g. external x-ray or fluoroscopy. Thus, higher concentrations of the treatment modality at the target with less side-effects are achieved. The removable stent of the present invention lends itself very well to such use, due to the combination of good structural support, non-invasive and convenient removal without contacting the treatment site with an external object, control of treatment site and control of duration of treatment.

The tubular body of the removable stent may have any dimensions, depending on its intended use. Preferably, the tubular body has a diameter in the range 0.5-10 cm. Further, the tubular body preferably has a length in the range 1.0-40 cm.

In addition to the above-discussed possible uses of the removal stent, the removable stent may also be used for many other purposes. For example, it is possible to use the removable stent as a supporting stent in combination with an expandable balloon for treating aneurysms. In particular, it is possible to use the new removable stent as the supporting stent in the stent device disclosed in U.S. application Ser. No. 12/457,664 and PCT application PCT/EP2009/057586 by the same applicant and the same inventors, said applications hereby incorporated in their entirety by reference.

According to another aspect of the invention there is provided a method for producing a removable stent, the method comprising the steps: forming at least one continuous thread into interconnected loops, thereby forming a porous tubular body; and providing a reversible bind-off at one end of the tubular body, mechanically securing each loop at said end of the tubular body apart from a single releasable loop.

Specific features and advantages in relation to this second aspect of the invention essentially follow the discussion of the first aspect of the invention above.

The forming of at least one continuous thread into interconnected loops is preferably made by knitting. Further, it is preferred that the at least one continuous thread is of metal, and preferably a metal alloy.

As discussed above, it is preferred that the at least one continuous thread is further arranged to extend with a loose end from said single releasable loop, thereby enabling release of said reversible bind-off by pulling said loose end, and unraveling of the interconnected loops by further pulling of the loose end.

The method further preferably comprises mechanically securing the end of the tubular body being opposite to the end having the reversible bind-off by means of a cast-on.

The method further preferably comprises the step of providing at least one of a bioactive agent and a radioactive agent in or on at least part of at least one of the continuous threads. with at least one of. This provision can e.g. be made by means of coating or impregnating.

According to another aspect of the present invention, there is provided a stent for treatment of dissections, and in particular type A dissections, using a removable stent having a porosity allowing blood to flow through the walls of a tubular part of the stent, and a radial strength sufficient to reattach the separated membrane to its original location along the vessel wall. The method for using such a removable stent, the preferred porosity and sparsity of the walls of the tubular body, and other characteristic features of the removable stent preferably follows the discussion above and below. However, for this line of use, other types of removable stents may be used, having similar structural strength and porosity/sparsity. For example, the contractible stent disclosed in U.S. application Ser. No. 12/457,664 and PCT application PCT/EP2009/057586 by the same applicant and the same inventors may be used to this end, said applications hereby incorporated in their entirety by reference.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
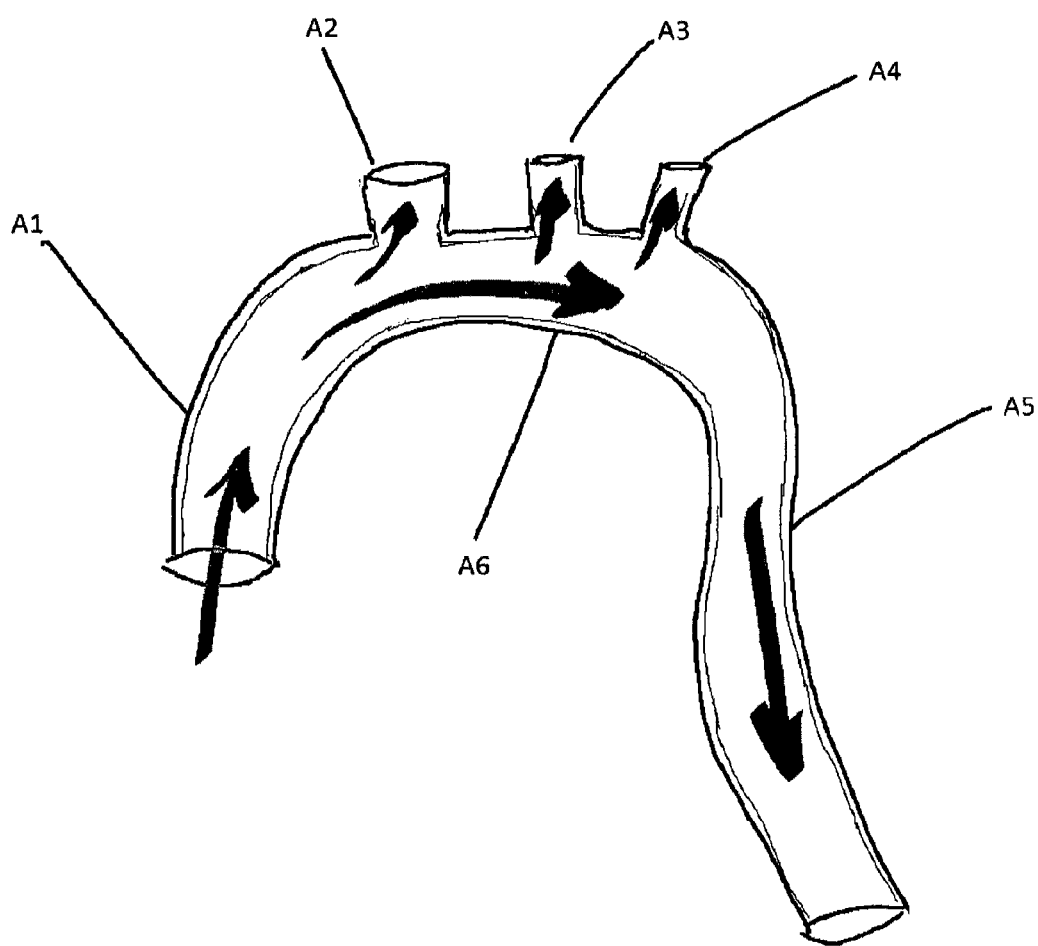
FIG. 1 is a schematic view of the normal flow through the aortic arch.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

Figure 5:
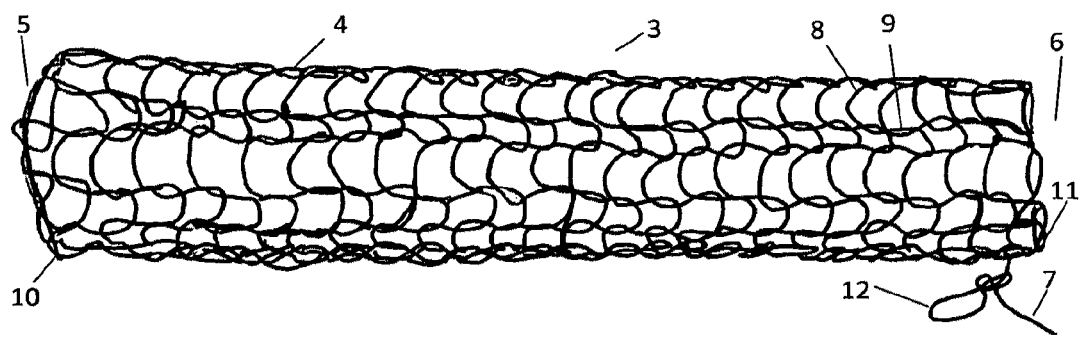
FIG. 5 is a detailed view of a removable stent according to an embodiment of the invention.

With reference to FIG. 5, a removable stent 3 according to one embodiment comprises a porous tubular body 4 formed by at least one continuous thread 8 arranged in interconnected loops 9. The loops are preferably connected by means of knitting. At a first end 5 of the tubular body, the outermost wale is preferably mechanically secured by a cast-on 10, securing all the loops at this end. At an opposite, second end 6, the outermost wale is secured by a reversible bind-off 11, mechanically securing each loop at this end of the tubular body apart from a single releasable loop 12. Thus, the end of the tubular body having the reversible bind-off comprises a wale in which all loops apart from one are mechanically secured by the reversible bind-off 11. Preferably, at least one additional mechanically secured intermediate loop 11' is arranged between the end wale and the releasable loop 12. In the illustrative example of FIG. 6, a plurality of such intermediate loops 11' are provided.

Figure 6:
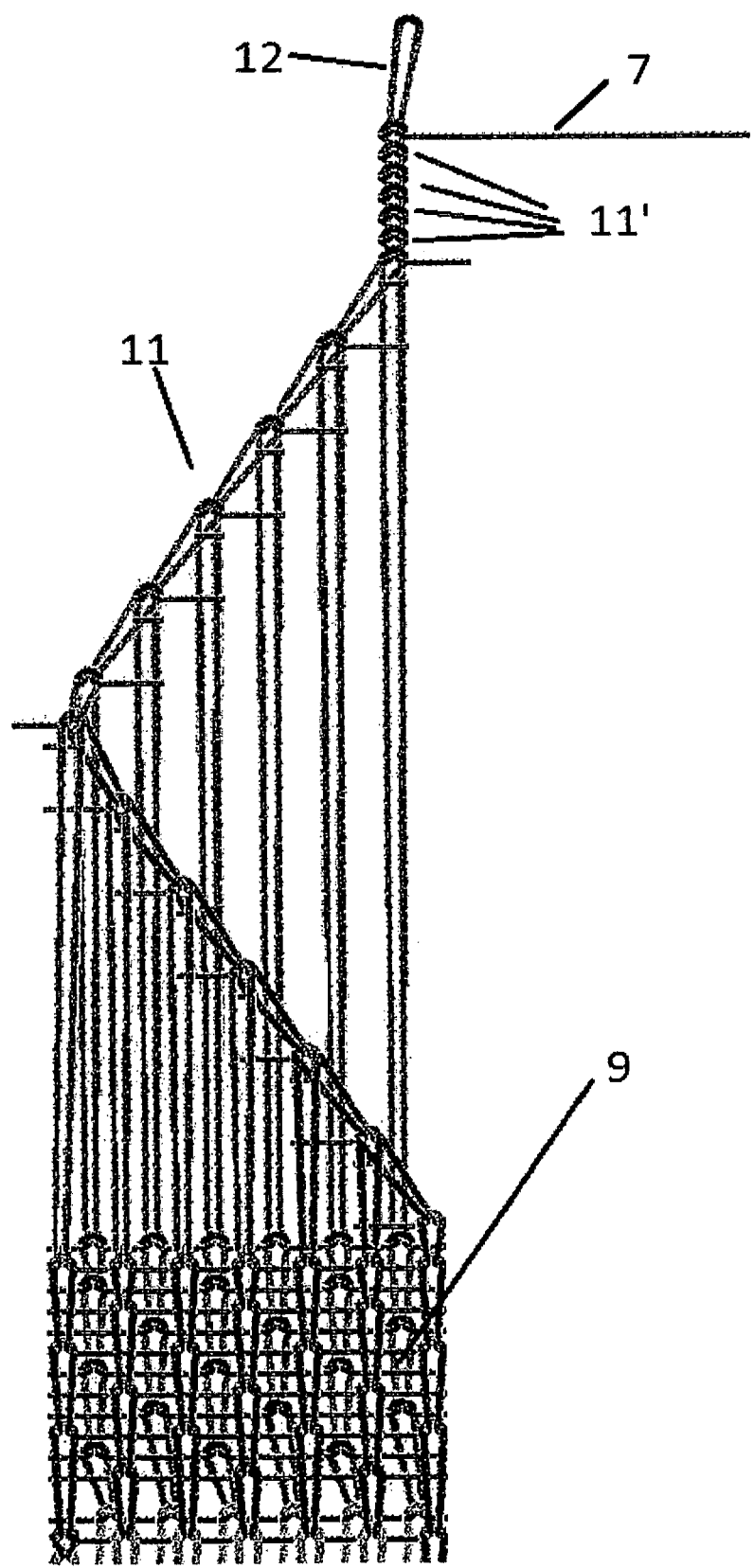
FIG. 6 is an example of a plain knitted stitch, interlock single jersey half gauge (1-1 technique), and its corresponding reversible bind-off.
Figure 7:
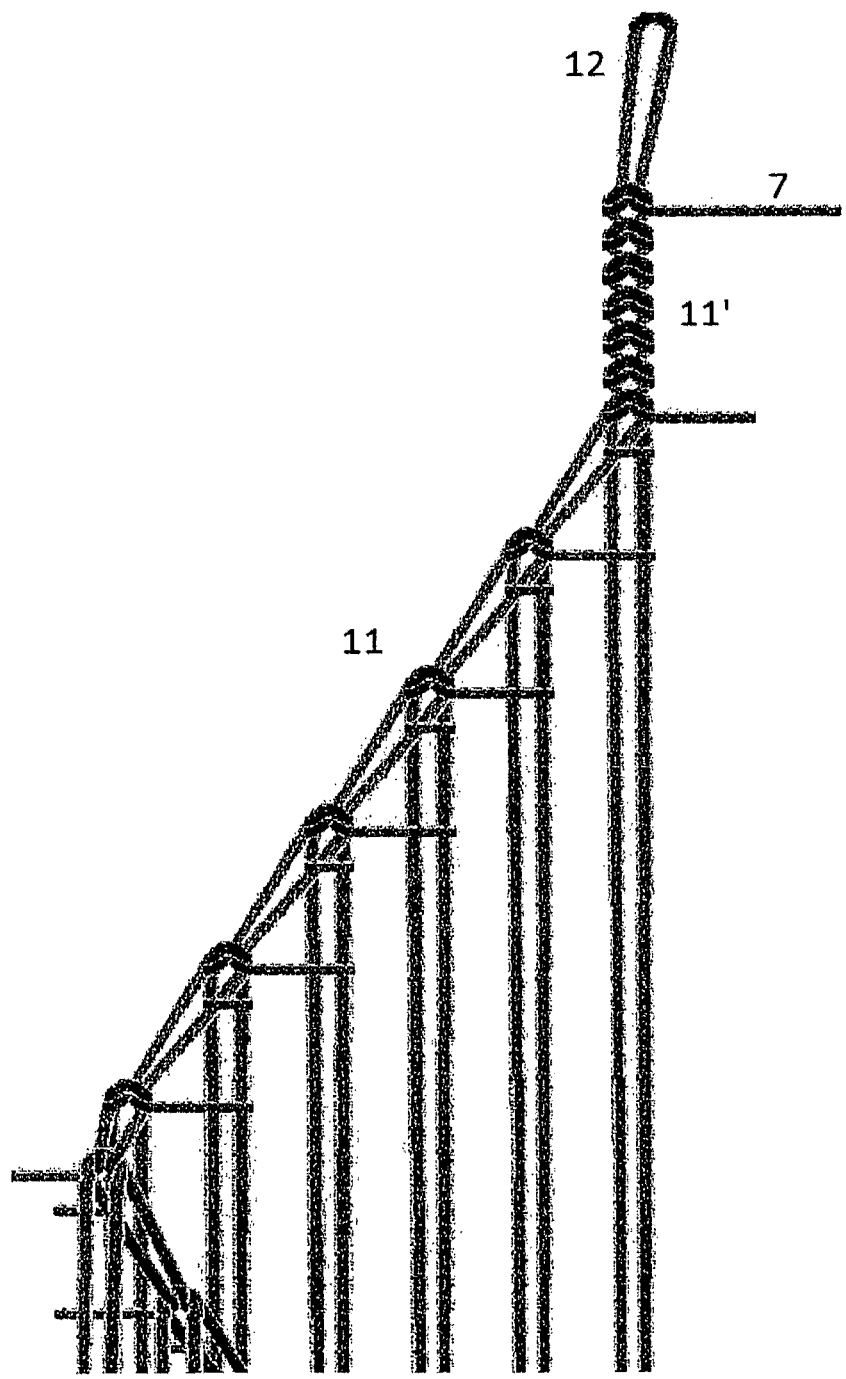
FIG. 7 is a schematic illustration of the reversible bind off shown in FIG. 6 in detail.

In general a bind-off always definitively and forever locks the knitted product. In a reversible bind off the last loop is not secured but left open and with an extension. An example of a reversible bind-off is illustrated in FIGS. 6 and 7. By pulling in the extension 7 the tubular body of the stent disintegrates (in this respect, reference is also made to FIG. 18). The presences of the reversible bind-off will secure the structure of the stent, while in use, but leaves the possibility to have a controlled disintegration at the time of choice. Thus with the reversible bind-off the structure is secured as in the more common traditional bind-off but the reversible bind-off includes the possibility to rip out the material, which is not possible with the traditional bind-off.

The at least one continuous thread preferably extends with a loose end 7 from the single releasable loop, thereby enabling release of the reversible bind-off by pulling said loose end, and unraveling of the interconnected loops by further pulling of the loose end. The loose end may extend to a position distant from the tubular body, and may even extend to a position outside the patient's body, which further facilitates the removal.

The continuous extension of the stent as a thread is at the same end as the reversible bind off. Pulling in the extension will release the reversible bind-off and the stent will disintegrate and form a single thread from which it was made.

The knitting stitches should preferably belong to the structure family of a plain knit but include the use of needle beds both in front and rear. The knit should be used for a tubular knit, which can be formed when the needles of the front needle bed are operated in separate sequences to those of the rear needle bed. When the separate knitting sequences are performed with the same carrier, the front and rear structures are joined into a tube. The knitting stitches is preferably at least one of: interlock single jersey, single interlock jersey, half gauge interlock single jersey, single jersey, single piquet, every third needle single jersey, and half gauge (1-1 technique).

By releasing this non-secured loop, the stent disintegrates into a single thread.

Due to the provision of the reversible bind-off, a mechanically stable tubular body is achieved, which retains it structure during use, and which is still very easy to remove, by releasing the reversible bind-off.

Further, the porosity of the tubular body of the stent permits blood flow to important blood vessels from the aorta through the sides of the stent. Preferably, the stent has big fenestrations with the ability to achieve free flow of blood through its sides.

Figure 24:
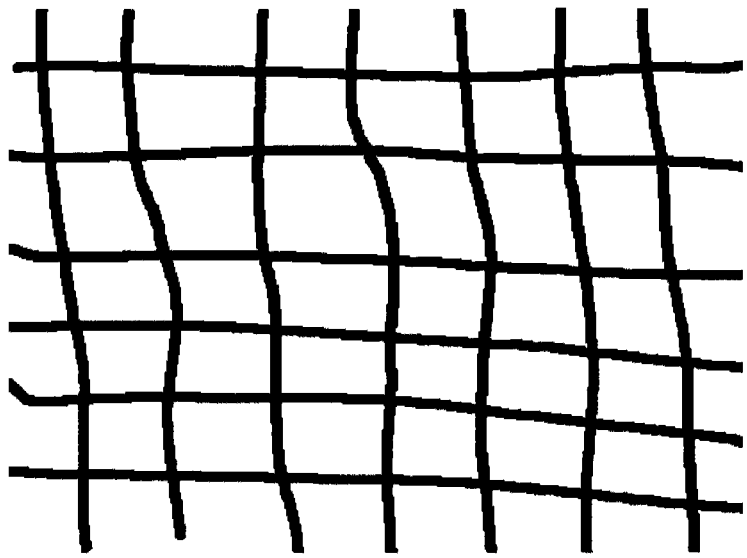
FIG. 24 is an exemplary illustration of a simplified stent surface, having a porosity of 0.8.

Preferably, the porosity of the tubular body of the stent is between 0.73 and 1. More preferably, the porosity is between 0.75 and 0.99. Most preferably, the porosity is between 0.8 and 0.98. We use the definition of the degree of porosity as the ratio between the area of the pores of a given patch of the stent and the area of the patch itself, as is illustrated in FIG. 24. One way to measure this is to estimate the number of white pixel in the whole picture and divide it with the total number of pixels. The porosity of the stent depicted in FIG. 5 can in such a way be estimated to 0.78.

Figure 8:
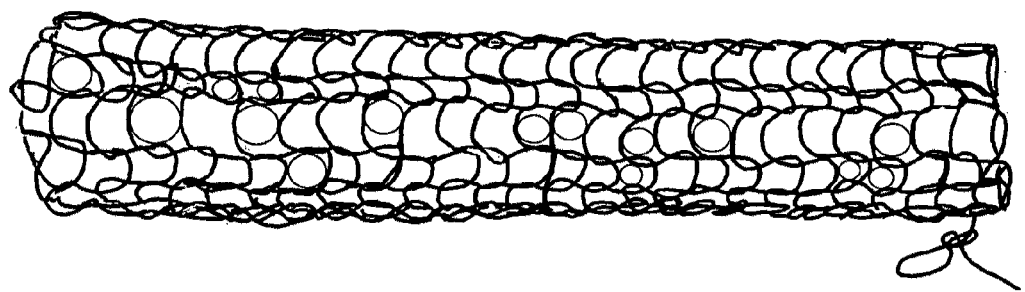
FIG. 8 is an illustration of the definition of sparsity.
Figure 25:
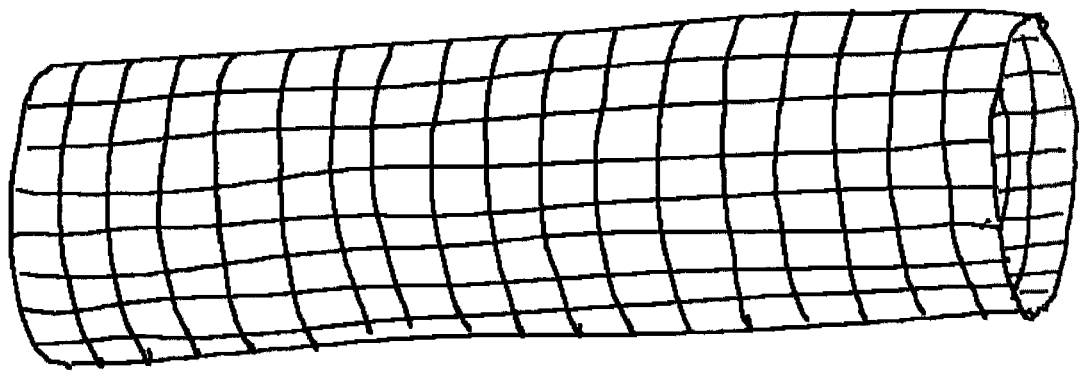
FIG. 25 is an exemplary illustration of a surface having a sparsity of about 0.15.

The sparsity of the tubular body of the stent is preferably in the range of 0.05 to 0.6. More preferably, the sparsity is in the range 0.07 to 0.5. Most preferably, the sparsity is in the range 0.10 to 0.4. Sparsity can be seen as a measure of the relation between the inflow area into the stent and the undisturbed outflow area through the stent-wall, as is illustrated in FIG. 25. Sparsity is defined as the ratio of diameters of a maximal circle in a typical open patch in the stent over the diameter of the stent. Here we can interpret typical, as the mean diameter of all patches, as seen in FIG. 8.

FIG. 24 is a schematic sketch of a, for illustration purpose, simplified stent surface. This configuration has a porosity of 0.8, which can be obtained by transforming the black and white drawing into a matrix and count the number of white pixels and divide with the total number of pixels of the patch.

FIG. 25 is an illustration of the sparsity which indicates the local amount of undisturbed flow through the stent wall. I.e. the ratio of the diameter of the largest disc that can be fitted in a "typical" opening (i.e. mean opening) in the projected stent wall and the diameter of the stent approximated as a cylinder. For ease of understanding, the simplified example in FIG. 25 has square like openings, with sides of 10 mm. If we use a thread diameter of 0.2 mm, the porosity would be $10^2/10.2^2=0.96$. The sparsity is here about 0.17.

Preferably, the removable stent is further expandable from a contracted insertion state to an expanded use state. Hereby, the stent may be contracted or compressed for easy insertion, and can then be expanded to its expanded state at the intended site of use.

The at least one continuous thread preferably comprises a material having a shape memory, and preferably at least one of a memory alloy, such as nitinol, and a memory polymer. Additionally or alternatively, the at least one continuous thread may comprise a material not having a shape memory, and preferably at least one of stainless steel, carbon, and plastic material.

The memory alloy is preferably one or several of: copper-zinc-aluminium-nickel, copper-aluminium-nickel, zinc-copper-gold-iron and nickel-titanium. The combination nickel-titanium is sometimes also named nitinol, which is very suitable for knitting. Examples include but are not limited to the following alloys: Ni—Mn—Ga, Fe—Mn—Si, Co—Ni—Al, Co—Ni—Ga, Ni—Fe—Ga, Ti—Pd in various concentrations, Ni—Ti (~55% Ni), Ni—Ti—Nb, Ag—Cd 44/49 at. % Cd, Au—Cd 46.5/50 at. % Cd, Cu—Al—Ni 14/14.5 wt. % Al and 3/4.5 wt. % Ni, Cu—Sn approx. 15 at. % Sn, Cu—Zn 38.5/41.5 wt. % Zn, Cu—Zn—X (X=Si, Al, Sn), Fe—Pt approx. 25 at. % Pt, Mn—Cu 5/35 at. % Cu, Pt alloys.

Preferred materials from the groups of shape memory polymers are: linear block polymers, thermoplastic polymers, cross linked polyurethan and polymers based on polyethylene terephthalate (PET), and polyethyleneoxide (PEO). However, the use of other shape memory polymers are also possible.

Furthermore, polymers have been widely used as delivery vehicles for drug coatings and could be combined with the stent of the present invention. These polymers include, but are not limited to, Poly-L-lactic acid (PLLA), polyglycolic acid (PGA), poly (D, L-lactide/glycolide) copolymer (PDLA), and polycaprolactone (PCL). Another proposed design is the hybrid stent, which combines a drug coating based on polymer, which carries the drug of interest combined with a backbone to enable strength and prevent recoil. Alternatively a stent with a backbone holding irradiation properties combined with coating based on polymer, which carries the drug of interest.

For the embodiments not having any self-expanding properties, materials like stainless steel, carbon, and any plastic material, which can execute enough radial strength can preferably be considered.

A number of oncological substances that might be of importance against cancer in the gastro-intestinal tract including the esophagus or in the hepatico-pancreatico-biliar system or in parenchymal cancer are available today and more will certainly come. Those which are potent but simultaneously have severe side-effects when administered in a systemic mode are especially suitable for local treatment under a controlled period of time. Bioactive agents which may be used to be administered by means of the removable stent include, but are not limited to: Cisplatin, mitomycin C, fluorouracil, cyclophosphamide, methotrexate, vincristine, gemcitabine, leucovorin, etoposide (FLv), adriamycin, streptozotocin, capecitabine, epirubicin, and oxaliplatin. However, the present invention is not limited to these substances but all potent chemotherapeutic substances where local treatment under a controlled period of time are plausible for use in the invention. In cancer in the gastro-intestinal tract including the esophagus or in the hepatico-pancreatico-biliar system a common mode of treatment is the combination of chemotherapy and irradiation. There are however situations when irradiation as the only local treatment is an alternative. Such an alternative is included with the present invention. Irradiation delivered locally is often entitled brachytherapy. High-dose rate (HDR) brachytherapy is when the rate of dose delivery exceeds 12 Gy hr-1. The use of different radionuclides/isotopes, with varying characteristics, in the treatment of e.g. cancer is known in the art and is within the scope of the present invention. Some examples of such radioactive agents, i.e. radiation sources, include, but are not limited to: Caesium-137, iridium-192, cobalt-60, Iodine-125, Palladium-103, Rhenium-188 and Ruthenium-106.

To activate the stent for local cancer treatment a gel-cover may be used, where the gel is a hydrogel that has previously been radioactive through a process in a cyclotron, accelerator or nuclear reactor. Furthermore, this gel coating can also carry non-radioactive medical agents, such as chemotherapy. Another more straightforward way to make the stent radioactive is to pick a suitable radioactivatable alloy and melt it together with the memory alloy in a controlled process. Thereafter the mixed alloy is placed in a nuclear reactor to receive neutron activation. Alternatively a radiation source, mentioned above, is from the beginning melted together with the memory alloy to skip the activation process. More detailed examples can be found in the above mentioned WO9951299, said document hereby incorporated by reference. However, as also mentioned above, the stent in WO9951299 is design to be permanent, thereby the isotopes chosen has to have relatively short half-times, and also have limited gamma radiation in order not to give a too high risk for side-effects. In the context of the current removable stent, since the stent will only be placed temporarily, there are other possibilities for using more aggressive isotopes and also higher ratio of the active alloy in a mixture.

The stent device is preferably compressed to a contracted state and located in a delivery sheath 2 before use. The use of a delivery sheath is per se known in the art, and is illustrated schematically in FIGS. 4 and 11.

Figure 11:
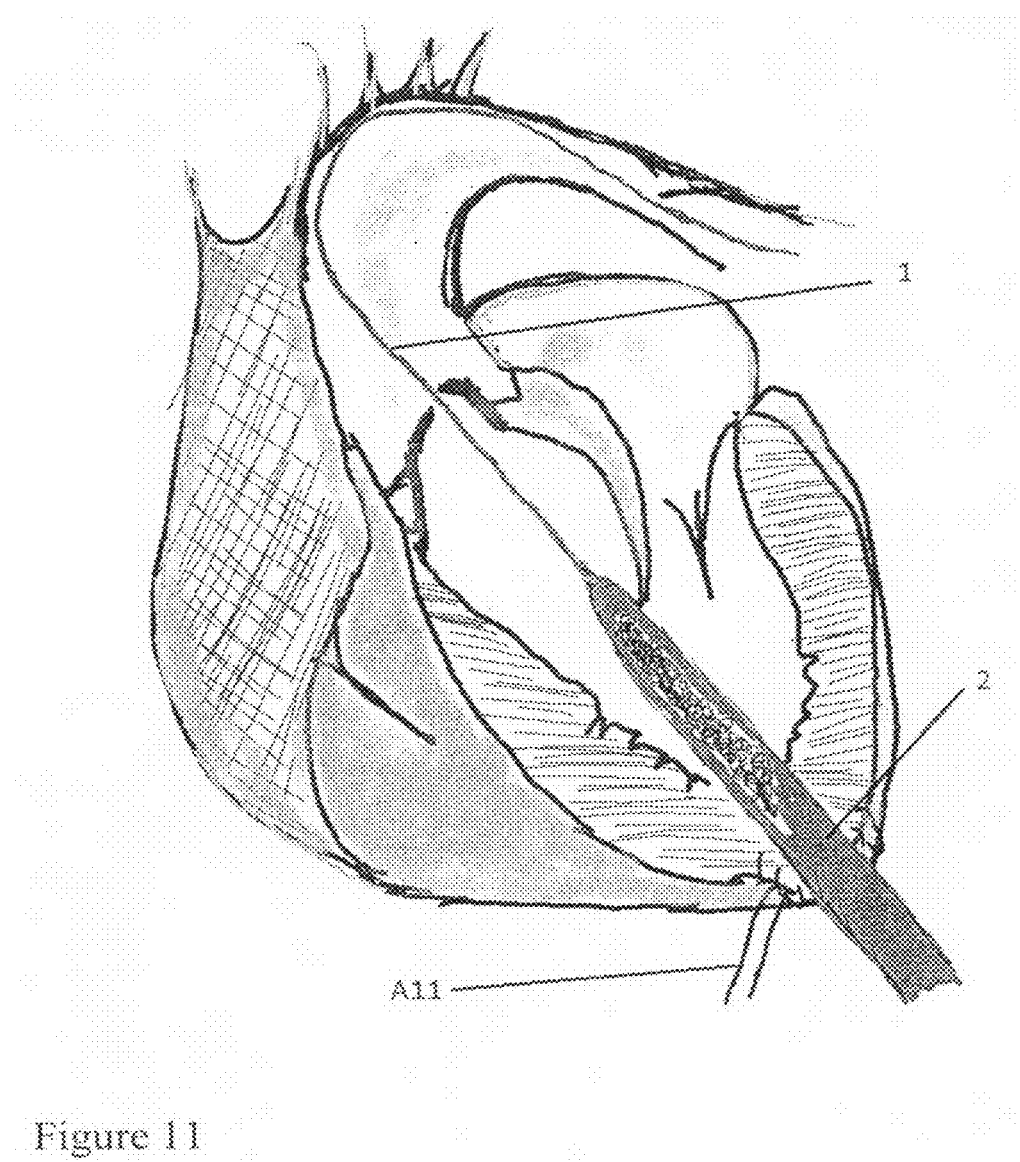
FIG. 11 is a schematic view demonstrating the transapical route where a delivery sheath including the removable stent slides on a guide wire. The entrance to the left heart ventricle is reached through a mini thoracotomy and the penetrating entry is secured by a purse string.

The stent can e.g. be inserted into the vascular system following puncturing of an artery, alternatively the heart, as is illustrated in FIG. 11, and positioning is achieved by means of a guide wire 1 followed by an introducer. The sheath 2 and the stent 3 preferably have a central channel with a diameter slightly larger than the diameter of the guide wire. The sheath and the stent enter the arterial tree by sliding on the guide wire located in the central channel. The position of the sheath and the stent are both possible to monitor with the help of x-ray. The sheath and the stent are positioned under fluoroscopic control in the area of intended treatment, such as the true pipe of the dissection. The stent is delivered by retracting the delivery sheath. In the case of a stent made of memory alloy it will then immediately expand to its predetermined size and design and e.g. press the membrane against the dissected wall, thereby occluding the false pipe. In the case of a stent not expandable through its material, it has to be expanded to its final size with the help of e.g. a balloon. In such a case the stent can in one embodiment be mounted on a deflated balloon (not shown) inside the delivery sheath. The stent will thereby keep its position by the shaft of the balloon after delivery from the sheath. In any case, the stent will keep its position when expanded by its radial strength against the vessel wall. In the latter case this is achieved after inflating, deflating and retrieval of the balloon.

The extension of the loose end of the stent can have such a length that it reaches the skin at the site of the introduction and puncture of the arterial tree/the heart. In this case the end is preferably fixed and covered by an adhesive bandage. Alternatively the loose end of the extension is left inside the arterial tree but then it has to be grabbed at removal. To this end, the loose end may be provided by gripping means, such as a snare at the end. Alternatively it can have its end in the subcutaneous tissue, which will secure the involuntary pulling of the extension and reduce the risk of infection keeping the advantage of no additional devices or intravascular interventions at removal. In this latter situation a small incision in local anesthesia will be performed and then pulling of the extension by hand to reach total removal as one single thread.

As already discussed, the removable stent may be used for treatment of dissections. Hereby, the tubular body is preferably provided with a radial strength enough to reattach the separated membrane to its original location along the vessel wall. Such use of the stent is illustrated in FIGS. 9, 10, 12, 13, 14, 15, 16 and 17; and where the tubular body preferably has walls which are permeable to blood, and most preferably allow free flow of blood through its structure. Such use of the stent is illustrated in FIGS. 13-16. After use, the stent can be removed by pulling in its loose end extension after the healing of the dissection, as is illustrated in FIG. 18.

FIG. 1 illustrates schematically the normal flow through the aorta, where A1 is the ascending aorta, A2 is the brachiocephalic artery, A3 is the left carotid artery, A4 is the left subclavian artery, A5 is the descending thoracic aorta and A6 is the aortic arch.

Figure 2:
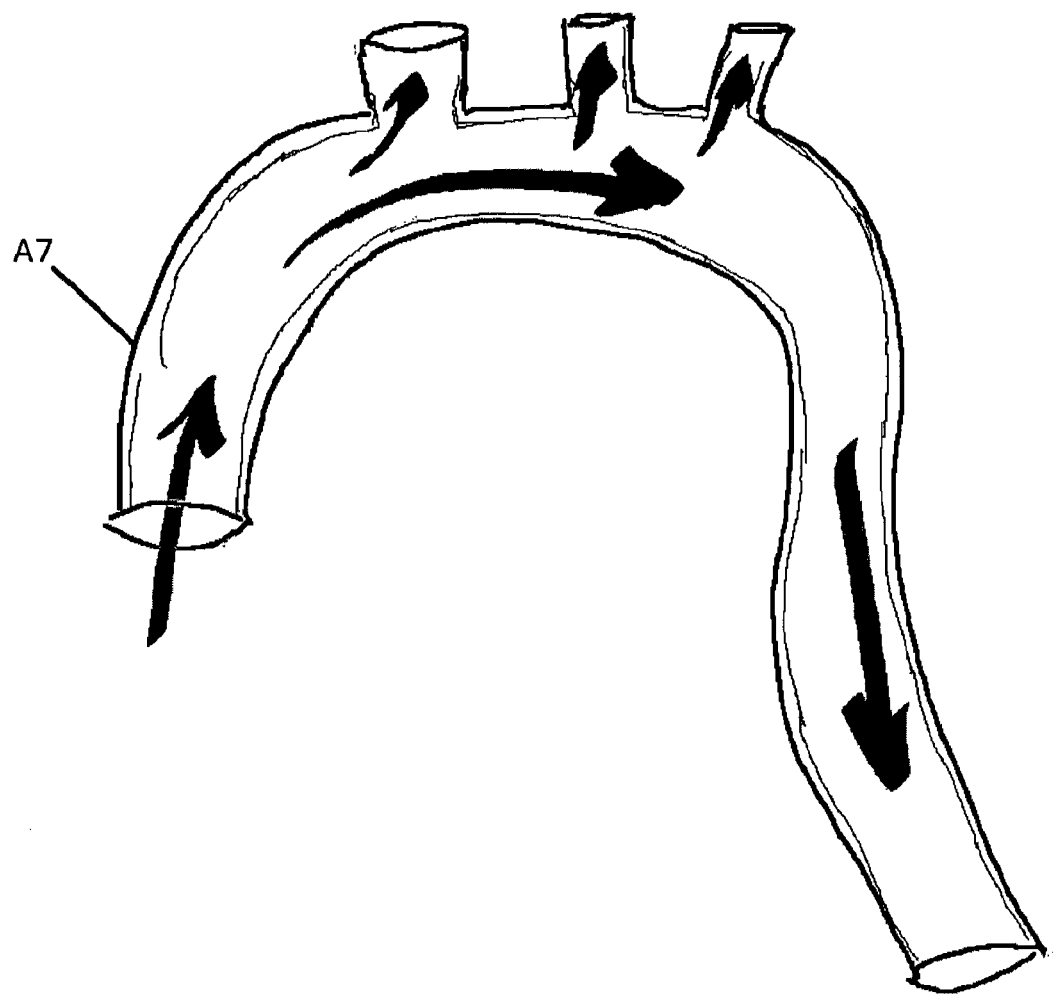
FIG. 2 is a schematic view demonstrating the development of a tear in the wall of the ascending aorta.

FIG. 2 illustrates schematically the development of a tear A7 in the wall of the ascending aorta.

Figure 3:
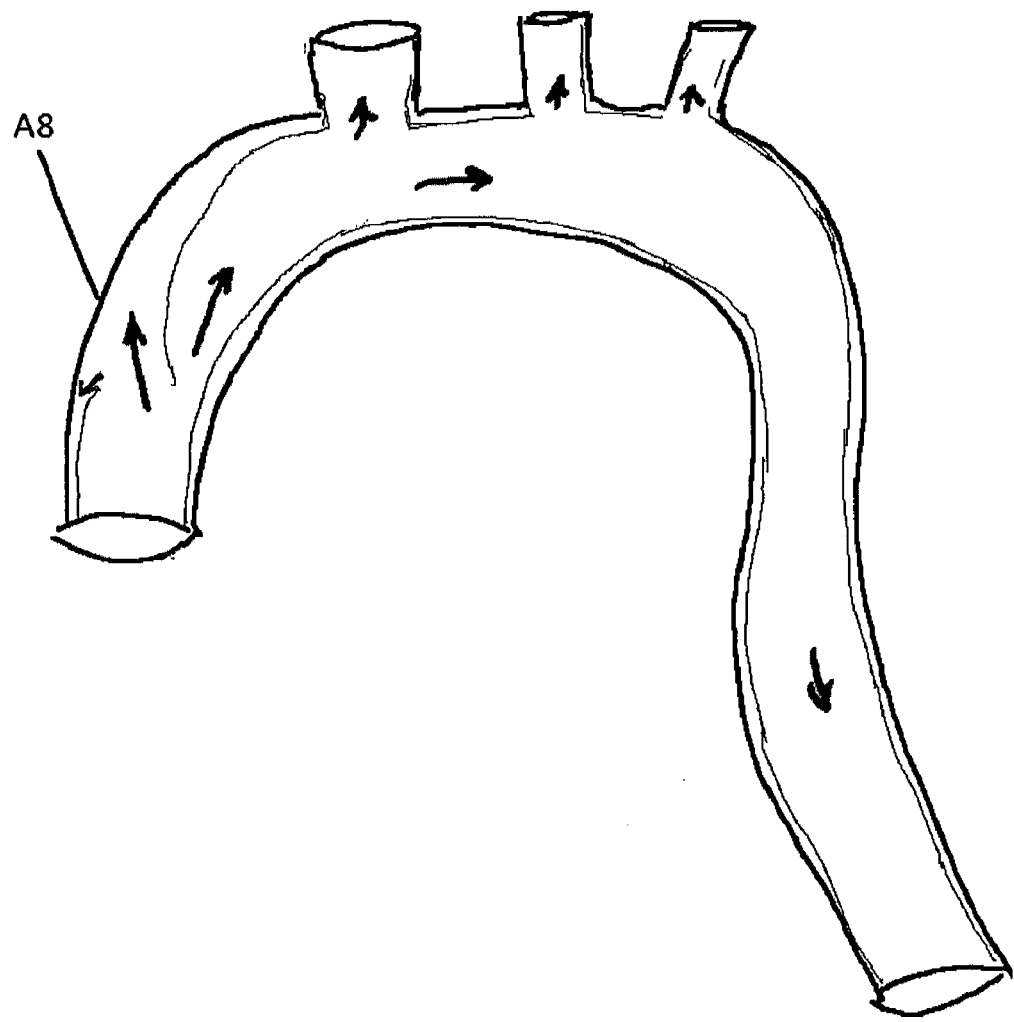
FIG. 3 is a schematic view demonstrates extension of the tear with flow into a false lumen, including a retrograde flow and split towards the heart.

FIG. 3 illustrates schematically and extension of the tear A8 with flow into a false lumen, including a retrograde flow and split towards the heart, i.e. a type A dissection.

Figure 4:
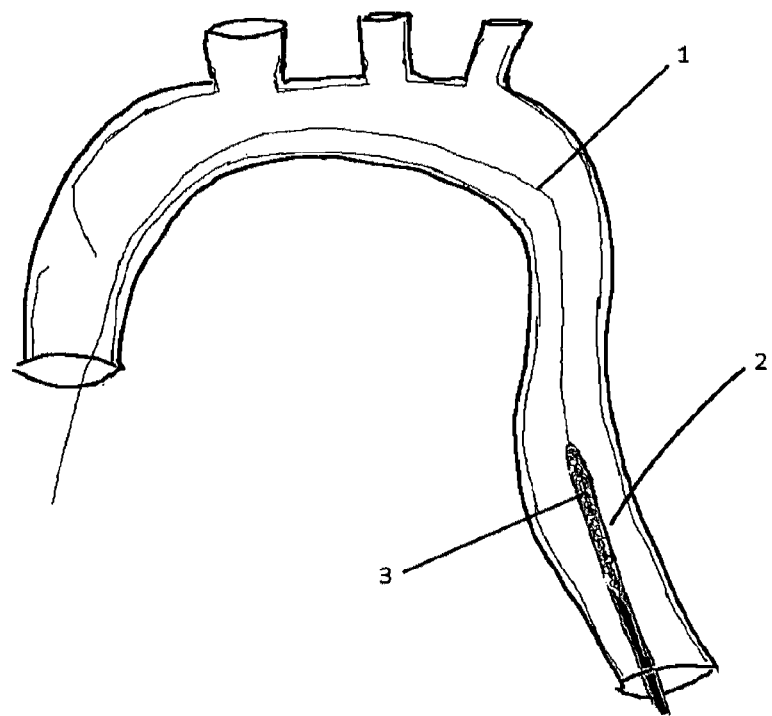
FIG. 4 is a schematic view demonstrating a delivery sheath, including the removable stent, sliding on a guide wire from a vascular access distal to area of interest.

FIG. 4 illustrates schematically a delivery sheath 2, including the removable stent 3, sliding on a guide wire 1 from a vascular access distal to area of interest.

Figure 9:
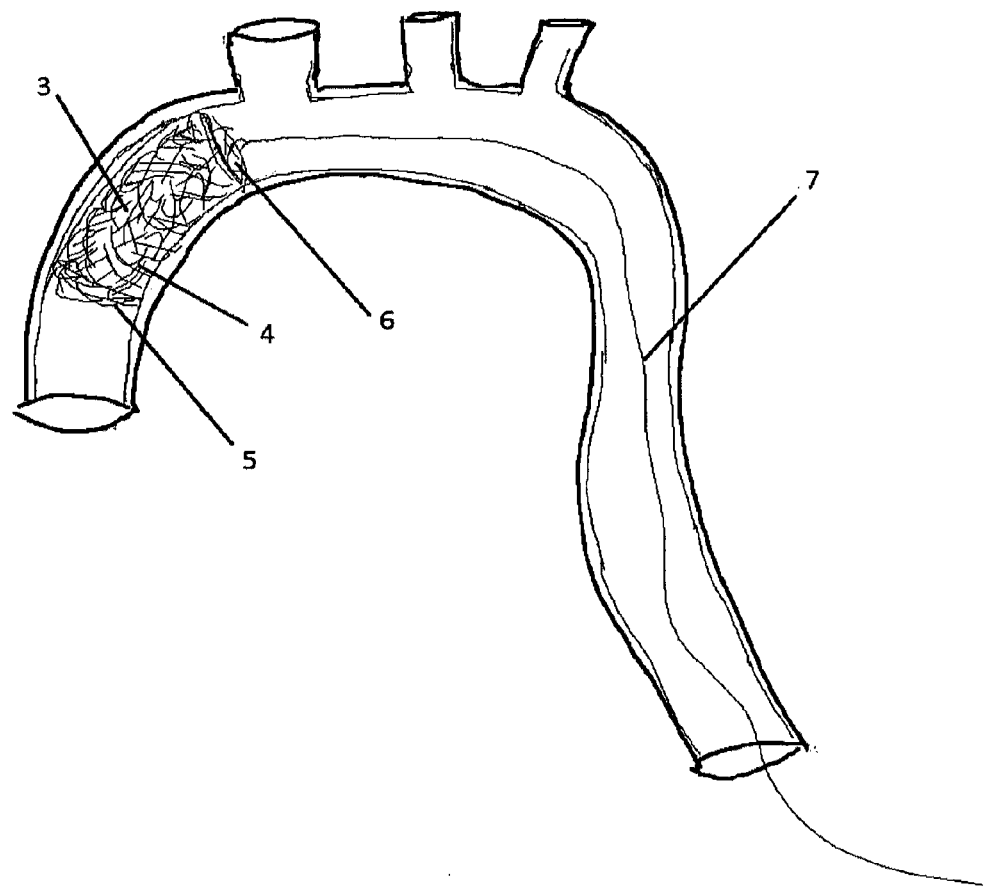
FIG. 9 is a schematic view demonstrating the removable stent being placed in the ascending aorta with its loose end extension beyond its tubular structure and at a distance far from the site of treatment.

FIG. 9 illustrates schematically the removable stent 3 placed in the ascending aorta with a loose end extension 7 beyond its tubular structure and at distance far from the site of treatment.

Figure 10:
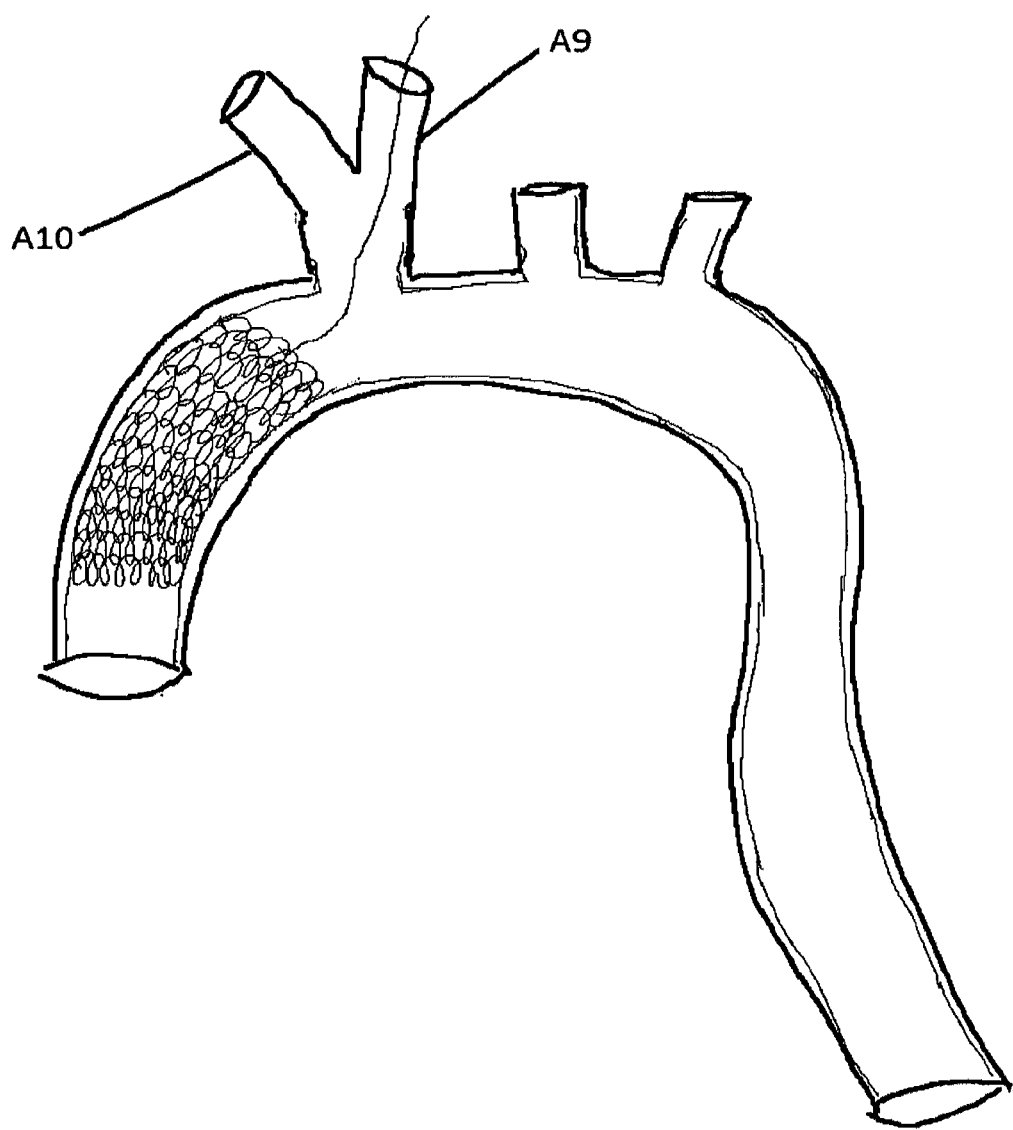
FIG. 10 is a schematic view demonstrating the same position of the removable stent in the ascending aorta but now with the extension through the right carotid artery.

FIG. 10 demonstrates schematically the same position of the removable stent in the ascending aorta but now with the extension through the right carotid artery, i.e. the alternative vascular access, A9. The right subclavian artery is here denominated A10.

Figure 13:
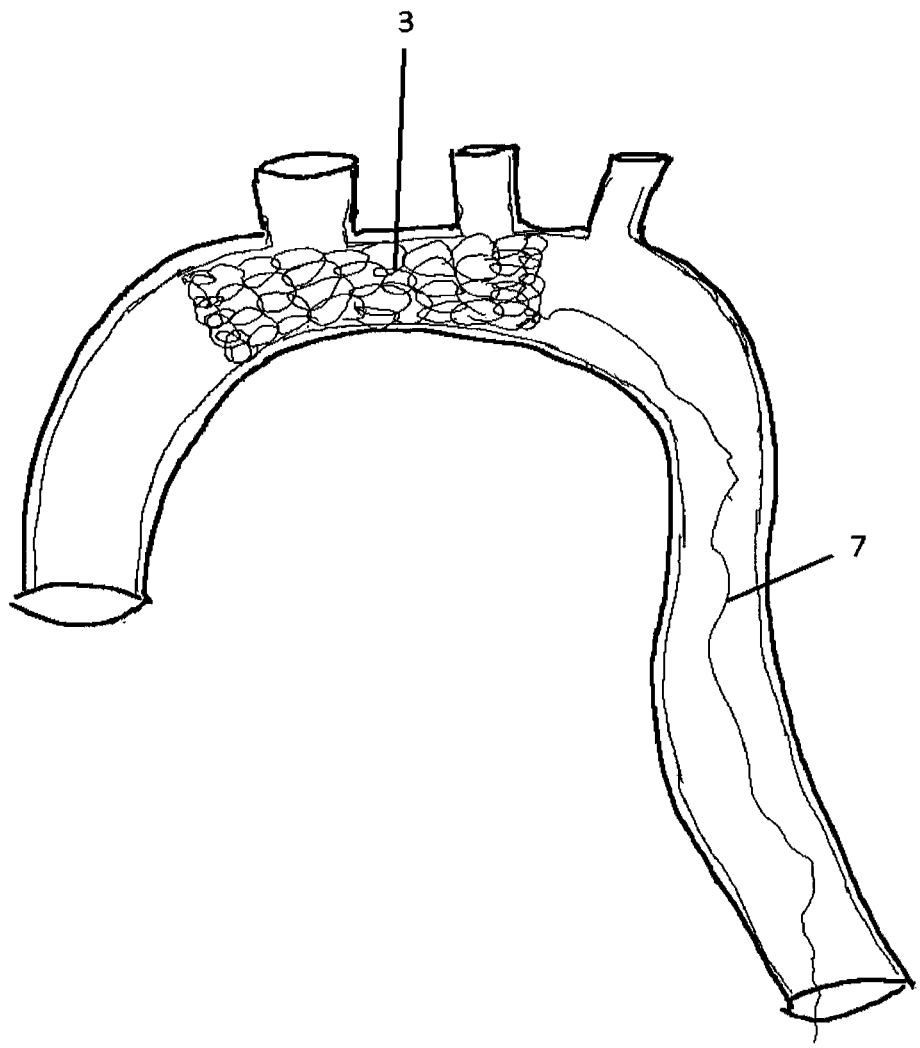
FIG. 13 is a schematic view demonstrating the removable stent covering the aortic arch, where a temporary stent can be placed preferably in combination with anticoagulation.

FIG. 13 demonstrates schematically the removable stent covering the aortic arch, where a temporary stent can be placed preferably in combination with anticoagulation.

Figure 14:
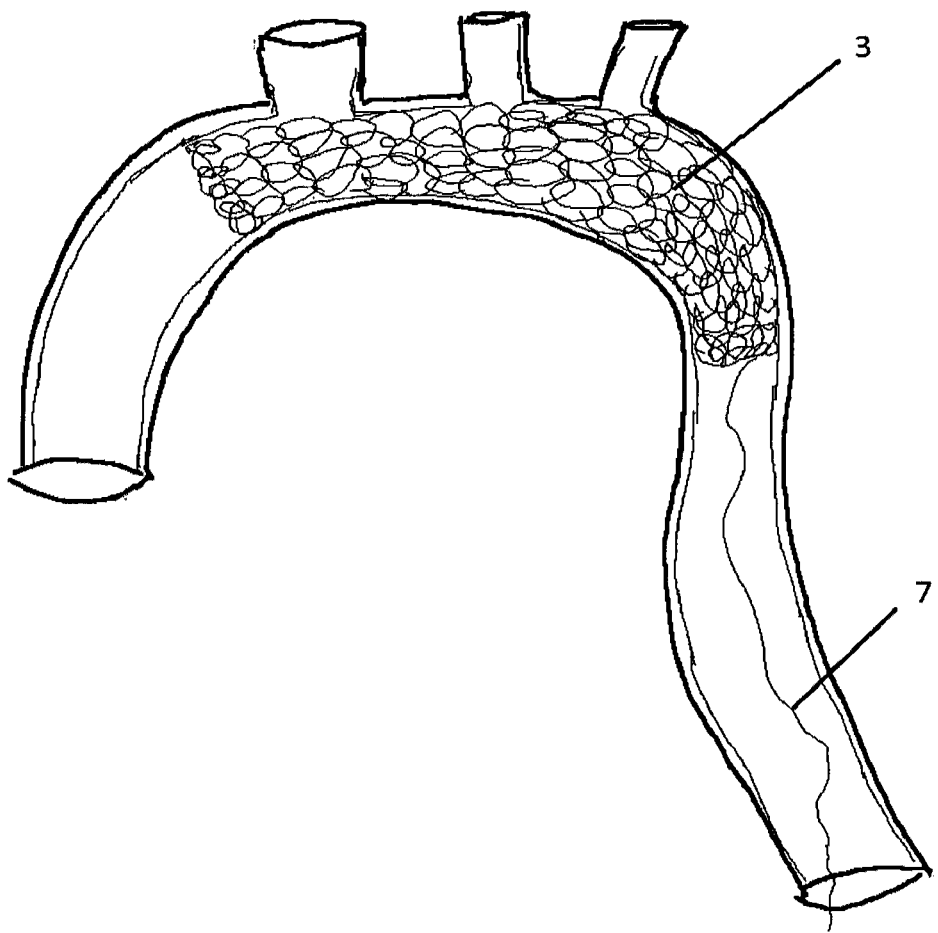
FIG. 14 is a schematic view demonstrating the removable stent covering the aortic arch but also including the ascending and descending aorta, where a temporary stent can be placed preferably in combination with anticoagulation.

FIG. 14 demonstrates schematically the removable stent covering the aortic arch but also including the ascending and descending aorta, where a temporary stent can be placed preferably in combination with anticoagulation.

Figure 15:
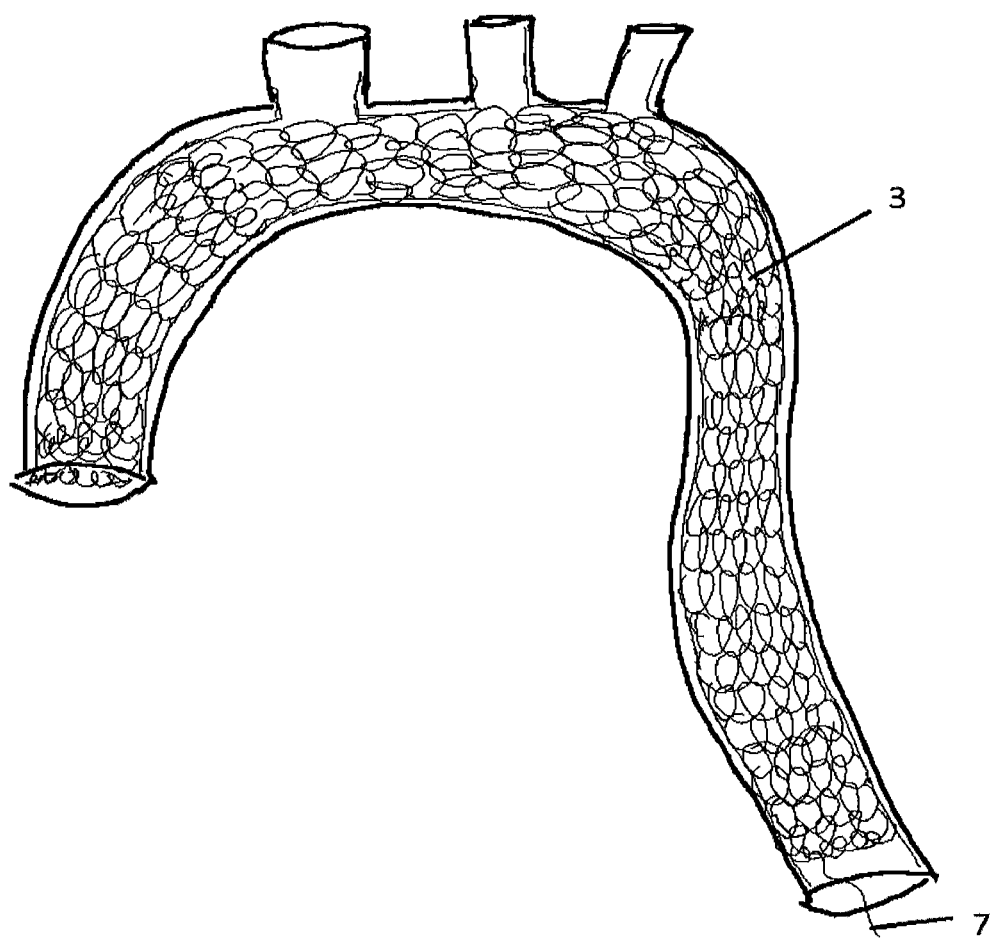
FIG. 15 is a schematic view demonstrating a longer removable stent covering the ascending aorta, aortic arch and descending aorta, where a temporary stent can be placed preferably in combination with anticoagulation.

FIG. 15 demonstrates schematically a longer removable stent covering the ascending aorta, aortic arch and descending aorta, where a temporary stent can be placed preferably in combination with anticoagulation.

Figure 16:
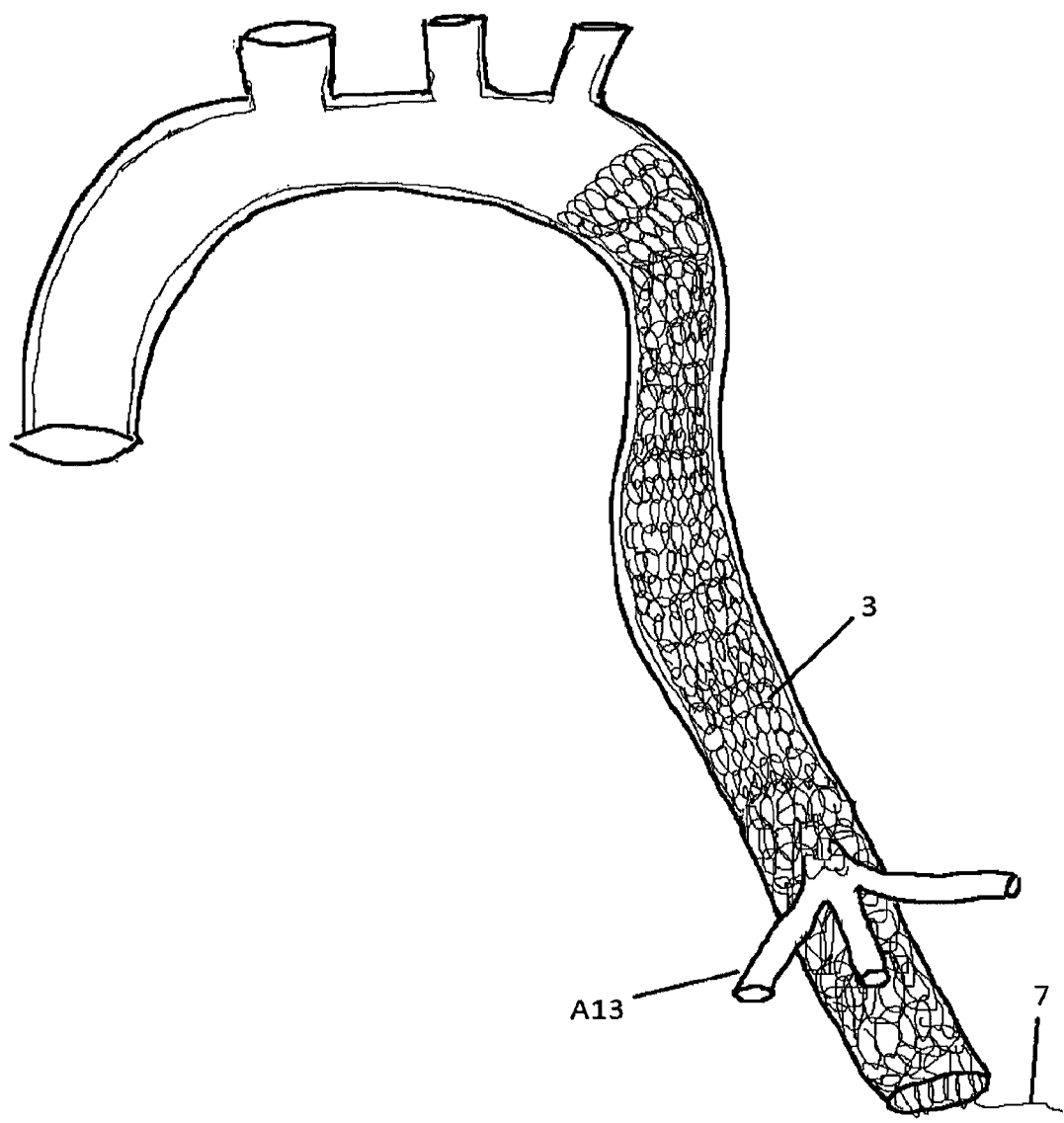
FIG. 16 is a schematic view demonstrating the removable stent covering the first part of the descending aorta which is the usual place for the main entry to the false lumen with a dissection type B. A coverage of the coeliac trunk is included.

FIG. 16 demonstrates schematically the removable stent covering the first part of the descending aorta which is the usual place for the main entry to the false lumen with a dissection type B. The length of the stent can vary. The removable stent has advantages when the length includes the take off of the visceral arteries.

Figure 17:
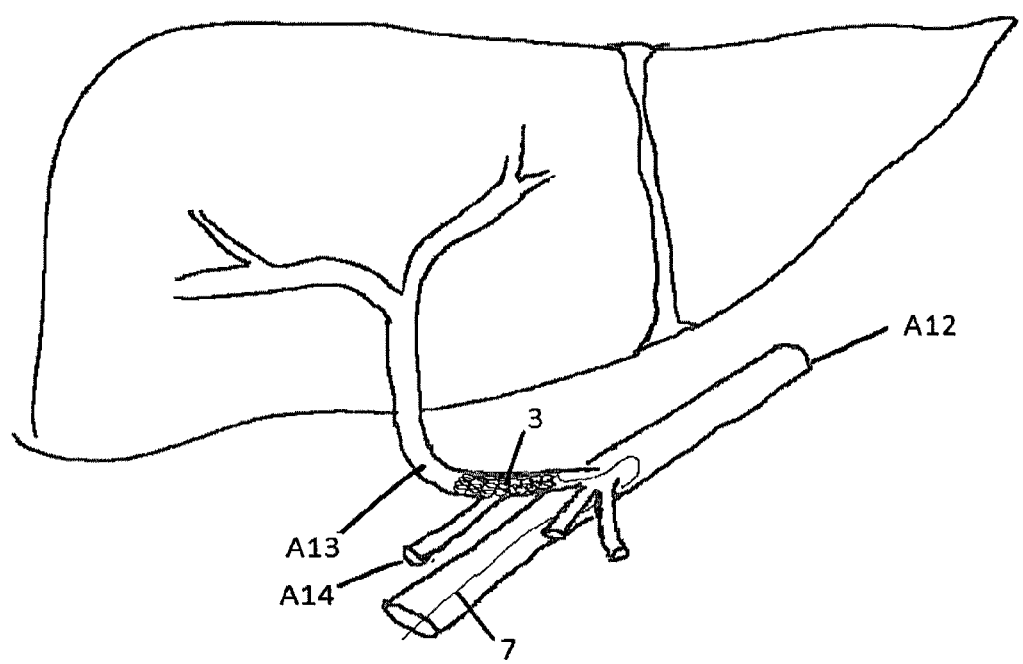
FIG. 17 is a schematic view demonstrating the removable stent covering a branch of the coeliac trunk.
Figure 18:
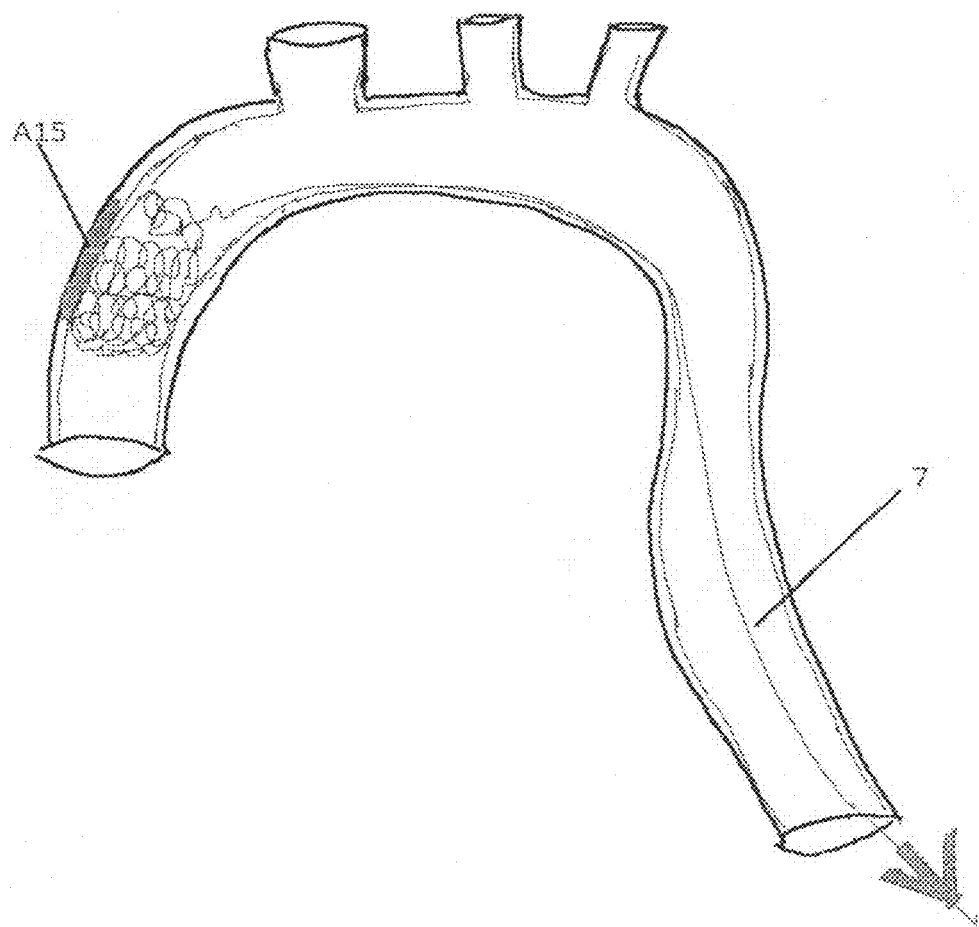
FIG. 18 is a schematic view demonstrating the removable stent when pulling in the loose end extension, disintegrating the structure via the reversible bind off.

FIG. 17 demonstrates the removable stent covering a branch of the coeliac trunk. Here the aorta is denominated A12, the gastroduodenal artery A14, and the proper hepatic artery A13.

FIG. 18 demonstrates schematically the removable stent when pulling in the loose end extension disintegrates the structure via the reversible bind off. The healed area is denominated A15.

The free flow of blood together with its temporary use will make it possible to position the stent in important locations, not previously suitable for stent treatment. An example is across the orifices of the vessels that take off from the aortic arch, as is illustrated in FIGS. 13-15. Such a suggested approach might need simultaneous and aggressive anticoagulation therapy as is per se known in the art. The stent preferably remains in its position until the wound-healing mechanism in the vessel wall has attached the split membrane to its original position. The removal of the stent will be achieved by pulling in its loose end extension, e.g. positioned at the skin surface, as illustrated in FIG. 18. Alternatively, removal may be accomplished by grabbing the end of the loose end extension in the arterial tree e.g. with a snare after puncturing an artery in a similar manner as described above. Pulling in the extension will make the stent disintegrate to one single thread. Thus, the present invention is consistent with the above discussed principles being a less traumatic but still invasive alternative for life-threatening dissections. This is an alternative that in an initial phase can be considered for patients not fit for big thoracic operations. It is temporary but the time for treatment is under control. It is a support during a natural healing process. Because of its temporary use it can be placed in positions, where stents have not been placed before. Adjunctive anticoagulation might be considered to reduce the risk for clot formation.

The removable stent may also be used for local treatment of diseases such as cancer in the gastrointestinal tract or any location which can be reached through a tubular system. The removable stent described in this invention is a suitable carrier for bioactive and/or radioactive agents, either by carrying the modalities as coatings or as an integrated part of the material. Due to the easy removability of the stent, the treatment will be local and the time for treatment can be precisely controlled. Further, precise positioning of the stent can be achieved by e.g. external x-ray or fluoroscopy. Thus, higher concentrations of the treatment modality at the target with less side-effects are achieved. The removable stent of the present invention lends itself very well to such use, due to the combination of good structural support, non-invasive and convenient removal without contacting the treatment site with an external object, control of treatment site and control of duration of treatment.

In this line of use, the tubular body is preferably provided with a radial strength enough to keep a certain position in tubular structures, Further, the tubular body is preferably at least partly covered with active substances and/or carries radioactive agents.

As stated above there are a number of oncological substances and irradiation sources which have shown partial effect against cancer in the gastro-intestinal tract including the esophagus or in the hepatico-pancreatico-biliary system or parenchymal cancer.

In this line of use, the stent device is preferably compressed and located in a delivery sheath 2 before use. With the help of endoscopic devices the stent may be introduced through the mouth or the nostrils into the gastro-intestinal system including esophagus and the hepatico-pancreatico-biliary systems. Such use is illustrated schematically in FIGS. 19-22. The stent is delivered compressed and located in a delivery sheath through the working channel of the endoscopic device. Under direct vision through the endoscopic device with or without x-ray support the stent is delivered at the target site. The stent is delivered by retracting the delivery sheath. In the case of a stent made of memory alloy it will then immediately expand and press against the surrounding walls. In the case of a stent made of a material or design, which is not self-expandable, the stent has to be expanded to its size with the help of e.g. a balloon. In such a case the stent can in one embodiment be mounted on a deflated balloon inside the delivery sheath. The stent will thereby keep its position by the shaft of the balloon after delivery from the sheath. In any case, the stent will keep its position when expanded by its radial strength against the walls. In the latter case this is achieved after inflating, deflating and retrieval of the balloon.

Figure 19:
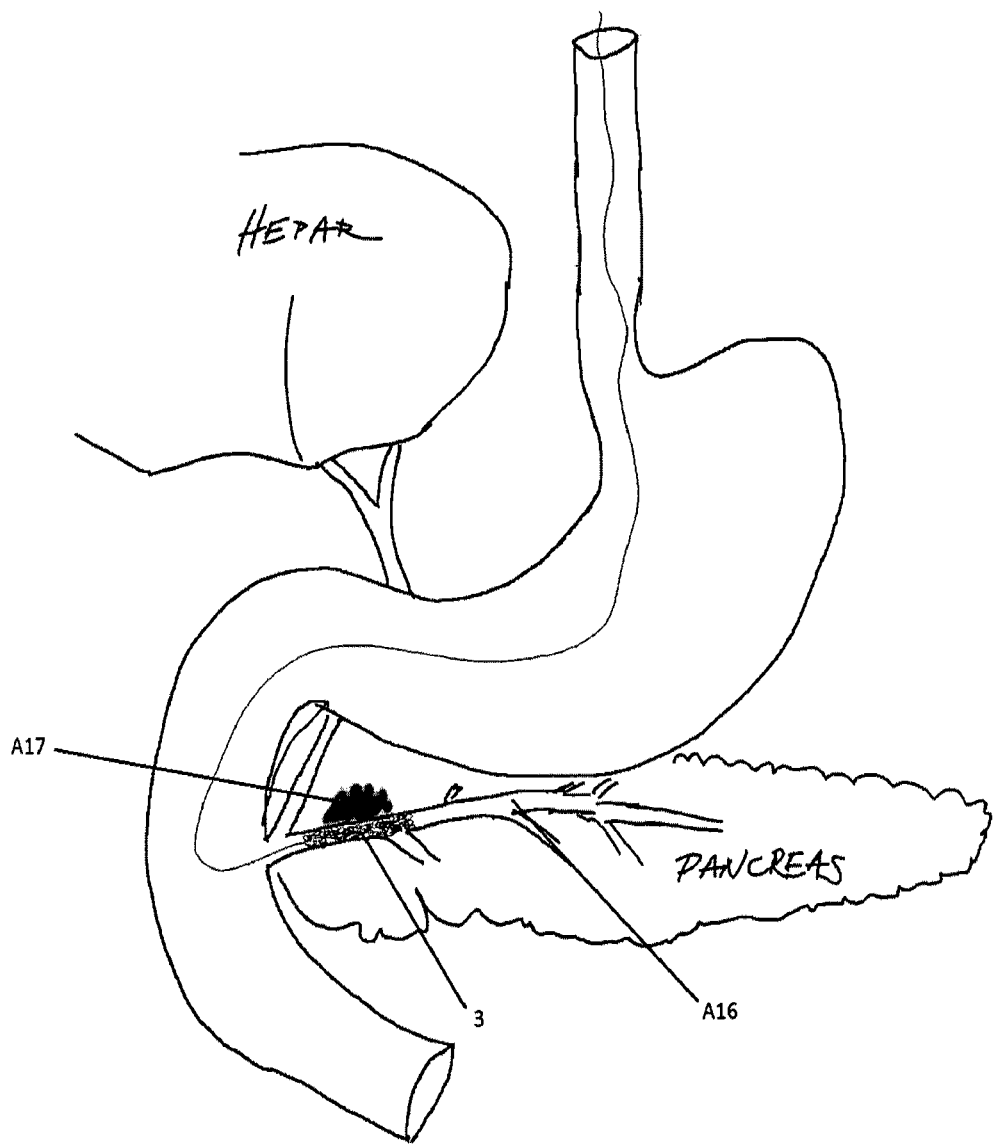
FIG. 19 is a schematic view demonstrating the position of the removable stent in the pancreatic duct. The stent can carry chemotherapeutic substances or irradiation or both to treat a pancreatic tumor.

FIG. 19 demonstrates the position of the removable stent 3 in the pancreatic duct A16. The stent can carry chemotherapeutic substances or irradiation or both to treat a pancreatic tumor A17.

Figure 20:
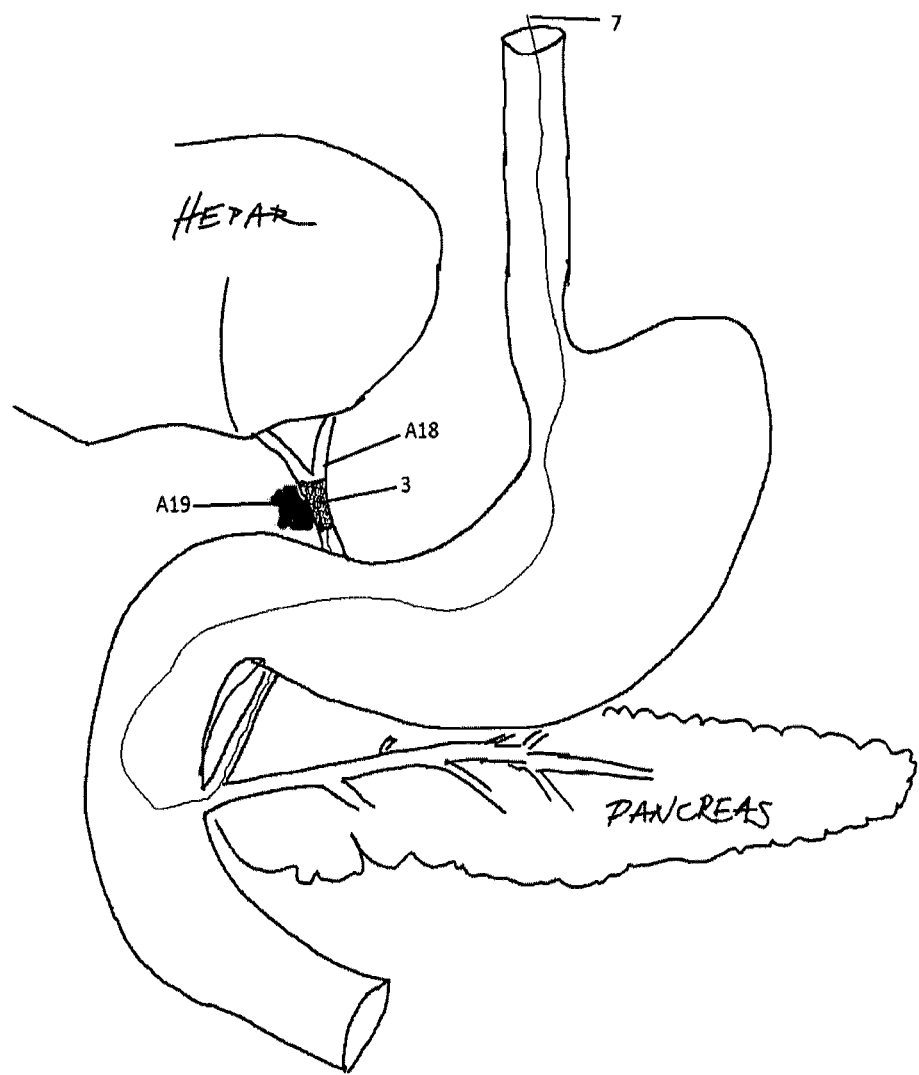
FIG. 20 is a schematic view demonstrating the position of the removable stent in the biliary tree. The stent can carry chemotherapeutic substances or irradiation or both to treat a biliary duct tumor.

FIG. 20 demonstrates the position of the removable stent 3 in the biliary tree A18. The stent can carry chemotherapeutic substances or irradiation or both to treat a biliary duct tumor A19.

Figure 21:
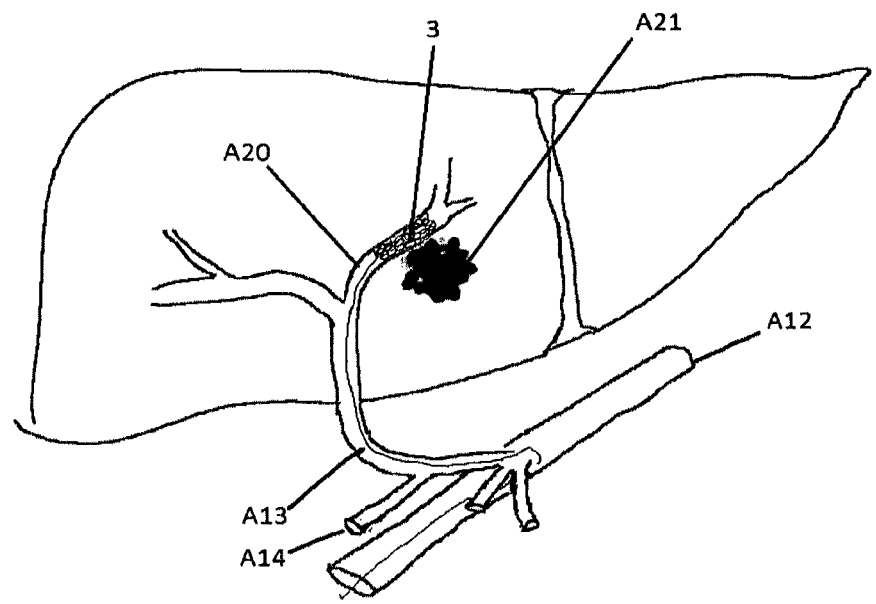
FIG. 21 is a schematic view demonstrating the position of the removable stent in the left liver artery which has been reached through the celiac trunk. It treats a parenchymal liver cancer. It is a schematic view showing an example of the possibility to treat other tissue than the tubular system used for delivery.
Figure 22:
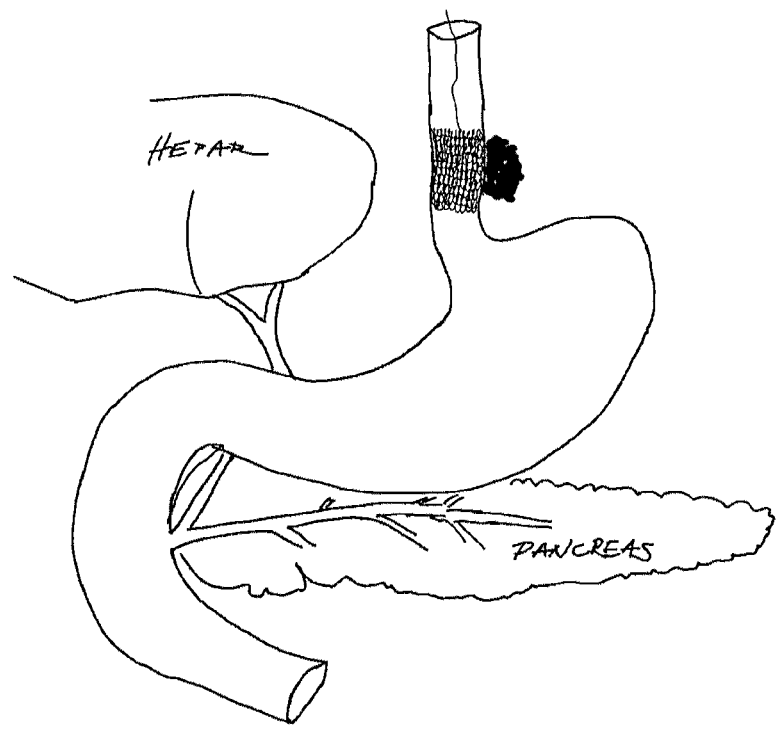
FIG. 22 is a schematic view demonstrating the position of the removable stent in the distal esophagus. The stent can carry chemotherapeutic substances or irradiation or both to treat a tumor in esophagus.

FIG. 21 demonstrates the position of the removable stent 3 in the left liver artery A20 which has been reached through the celiac trunk. It treats a parenchymal liver cancer A21. It shows an example of the possibility to treat other tissue than the tubular system used for delivery.

In case of a very obstructing growth of cancer positioning of a guide wire through the tumor mass might be needed. For such use, the sheath and the stent preferably have a central channel with a diameter slightly larger than the diameter of the guide wire. The sheath 2 and the stent will in such a case enter the target for treatment by sliding on the guide wire, which is located in the central channel and through the tumor mass. The same principles can be applied for bronchial or pulmonary cancer in which the stent is placed in any generation of the pulmonary tree with the help of a bronchoscope, as is illustrated schematically in FIG. 23.

Figure 23:
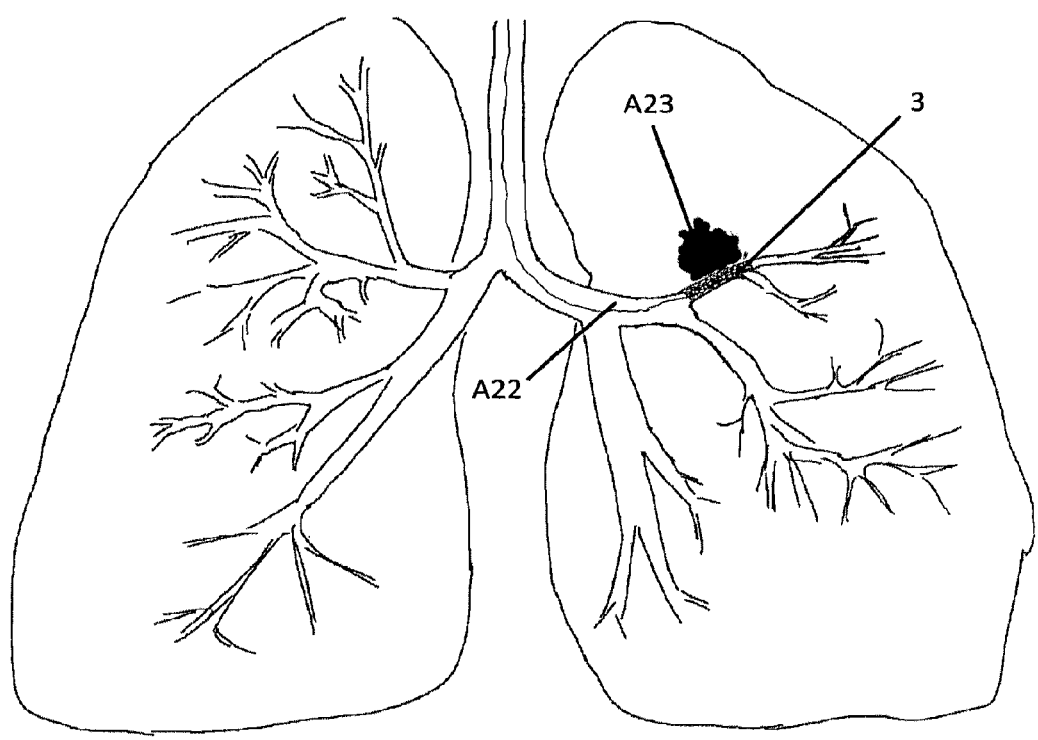
FIG. 23 is a schematic view demonstrating the position of the removable stent in the left bronchial tree to treat a tumor in the upper left pulmonary lobe.

FIG. 23 demonstrates the position of the removable stent 3 in the left bronchial tree A22 to treat a tumor A23 in the upper left pulmonary lobe.

Even if the mentioned deliveries will be executed with the help of a device and under direct vision, it can be combined with the possibility of external x-ray for control of final position and position during the time of treatment. The stent can also be delivered through the vascular system as described above but used as therapy against parenchymal cancer. As example the stent can use the route—aorta, common hepatic artery, proper hepatic artery, either the right or the left hepatic artery and their peripheral generations inside the liver to treat liver cancer. Such a use is illustrated schematically in FIG. 21. Thus the cancer cells do not have their origin in the tubular system through which the stent is delivered and finally positioned. The removal of the stent in this latter case will be identical as described for dissections. The same principles can be used for other parenchymal organs e.g. the brain and also with the use of the venous system to reach the target.

Dependent on type of cancer, type of drug, dose of irradiation and location, the time during which the stent will remain in place will vary. When appropriate the stent will be removed by pulling in the extension, which will make the stent disintegrate to one single thread.

Thus, the present invention is consistent with the above discussed principles being a treatment for cancer with the characteristics of being local and where the time for treatment is under control and where types of cancer without present local treatment can be included. This gives the possibility to give a controlled treatment with increased dose of chemotherapy and irradiation alone or in combination with the potential of better effect with less side-effects. Furthermore the removal does not necessary need any extra instrument and will always be executed without any manipulation in the direct vicinity of the treated area, ending up with a thin thread.

The loose end extension can in one preferred embodiment be a connected single thread, or two or more single threads knitted in parallel from the location of the stent to the skin surface above the initial access to the arterial tree. As one example the extension thread can start at a delivered stent in the ascending aorta and have its end at the skin surface in the groin, in the case that the common femoral artery has been used for initial vascular access. The vascular access can vary for different purposes of the stent. For example, any place where pulses are felt can be used for arterial access. Examples are: the femoral artery, as is illustrated in FIGS. 4, 9, 13, 14, 15, 16, 17 the radial artery, the ulnar artery, the axillar artery or the carotid artery, as is illustrated in FIG. 10. Less convenient arterial access can be reach by the help of ultrasound, which covers non-palpable arteries. Ultrasound may also be used for venous access at any location for example in the neck or the groin.

Figure 12:
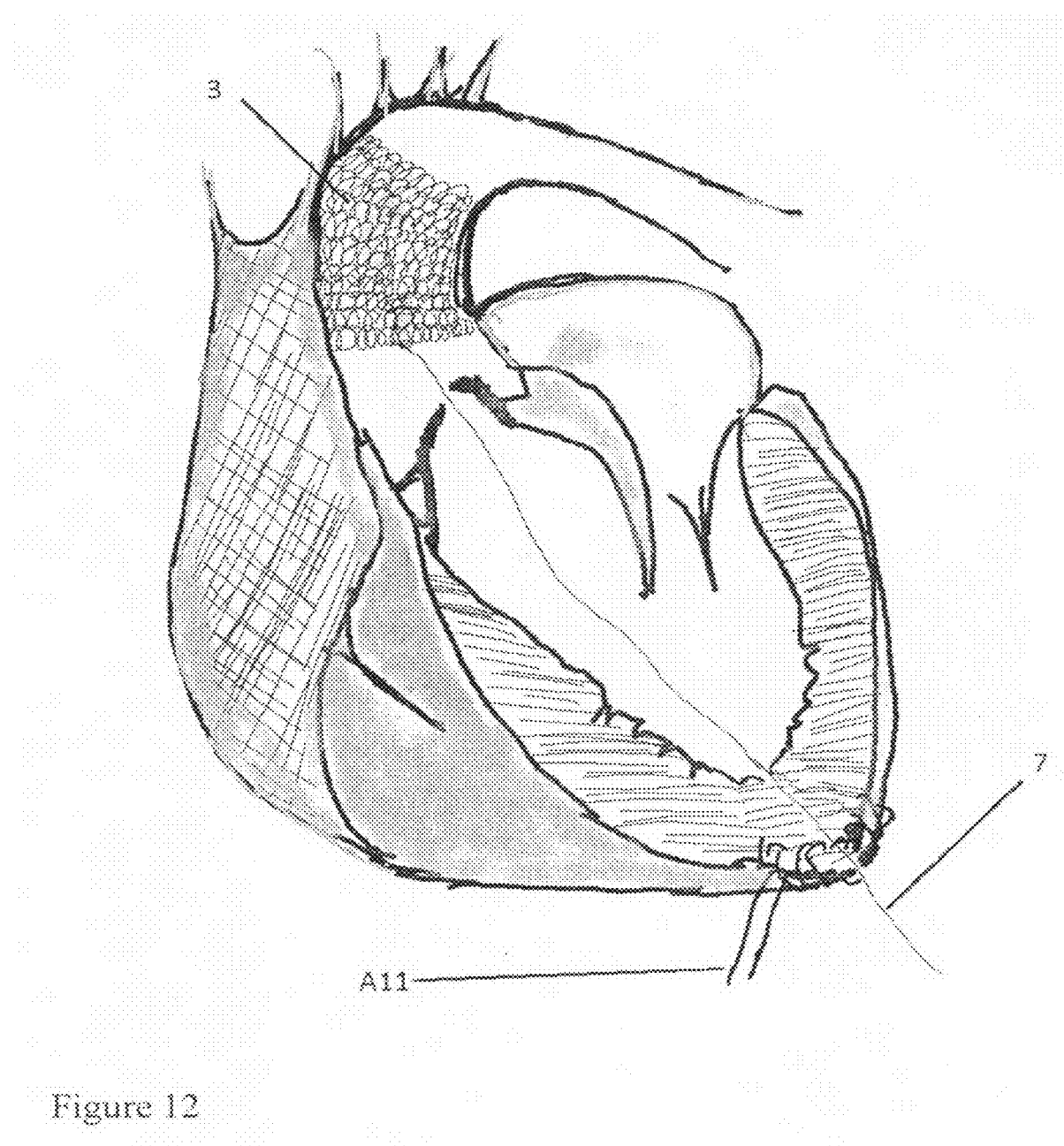
FIG. 12 is a schematic view demonstrating the removable stent covering the ascending aorta with the extension through the left ventricle and through the apical part of the heart. Still the extension thread is far apart from the treated area. The purse string is tied to secure the area of vascular access.

One preferred access for the treatment of the ascending aorta is the transapical route, illustrated in FIGS. 11 and 12. FIG. 11 demonstrates schematically the transapical route where a delivery sheath 2 including the removable stent on a guide wire 1. The entrance to the left heart ventricle is reached through a mini thoracotomy and the penetrating entry is secured by a purse string A11. FIG. 12 demonstrates the removable stent covering the ascending aorta with the extension through the left ventricle and through the apical part of the heart. Still the extension thread is far apart from the treated area. The purse string A11 is tied to secure the area of vascular access.

In this method of use, the device reaches the ascending aorta through a left ventricular transapical approach by using a left mini-thoracotomy. The introduction through the heart is secured through a purse string, which is tied when the delivery sheath is retracted. The extension thread of the stent, described above, which is of minimal diameter, can be left on the skin surfaces of the chest, upper abdomen and follow the route of the introduction. Thus be left through the wall of the left ventricle of the heart. The advantages of this method are the short distance and straight route to the area of treatment. It thereby lacks some dangers compared to using the femoral or carotid artery. Examples of such dangers are emboli to the brain or the leg, damage of the arterial wall by the mechanical manipulation, thromboses far away from the treated site.

If the end of the extension reaches the skin surface, the end has to be secured and covered with an adhesive bandage. In the example with access through the common femoral artery, the extension thread may be located inside the whole aorta, the iliac arteries on one side, the femoral artery, subcutaneous tissue and the skin surface.

Alternatively the end of the extension thread has such a length that it is located within the vascular tree after positioning of the stent. In such an alternative the vascular tree has to be punctured again at the time of removal and a snare, or something functionally similar, has to be introduced to grab the end of the extension. Pulling at the end of the extension with the help of the snare will as described above disintegrate the stent to the thread from which it was made. For convenient removal of the disintegrated stent and the snare from the vascular tree an additional docking sheath could be of value. However, such a docking sheath will preferably be introduced a relatively short distance into the vascular tree and far apart from the site of treatment. An advantage with the present invention is that it has a smooth removal without direct contact with any external devices during explantation. When the end of the extension of said stent is initially placed on the skin surface no additional devices are needed for removal. The stent will disintegrate to a single thread by simply pulling at the end placed at the skin surface. By further pulling the stent will be fully removed. Alternatively the extension can have its end in the subcutaneous tissue, which will secure the involuntary pulling of the extension and reduce the risk of infection keeping the advantage of no additional devices or intravascular interventions at removal. In this situation a small incision in local anesthesia will be performed and then pulling of the extension by hand to reach total removal as one single thread.

The continuous extension of the stent as a thread will be at the same end as the reversible bind-off. Pulling in the extension will release the reversible bind-off and the stent will disintegrate and form a single thread from which it was made. The extension can in one preferred embodiment in the case of cancer be a single thread from the location of the stent to the skin surface. An alternative is that the extension of the stent exits through a nostril and is fixed to the adjacent skin of the face. In such a case this very end is preferably secured and covered with an adhesive bandage at the skin surface. As one example the extension thread can start at a delivered stent in the common biliary duct, as illustrated in FIG. 20, and have its end at the skin surface in the face. In the given example the extension thread is located inside the biliary tract, duodenum, ventricle, esophagus, epipharynx, nose and the skin surface.

Alternatively the end of the extension thread has such a length that it is located within e.g. the gastro-intestinal tract including the esophagus or in the hepatico-pancreatico-biliar system or the pulmonary tract after positioning of the stent. In such an alternative, an endoscope/bronchoscope and a snare, or something functionally similar, is at the time of removal preferably introduced to grab the end of the extension and pull the end through the endoscope/bronchoscope, grab the end manually outside the endoscope/bronchoscope, remove the disintegrated stent and finally the endoscope/bronchoscope. When the end of the extension of said stent is initially placed on the skin surface no additional devices are needed for removal. The stent will disintegrate to a single thread by simply pulling at the end placed at the skin surface. By further pulling the stent will be fully removed.

The use of the removable stent as discussed above, its described delivery and removal, is consistent with the above discussed principles being a treatment for cancer in the gastro-intestinal tract including the esophagus or in the hepatico-pancreatico-biliar system or parenchymal cancer with the characteristics of being local and where the time for treatment is under control. This gives the possibility to give a controlled treatment with increased dose of chemotherapy and brachytherapy alone or in combination with the potential of better effect with less side-effects. Examples to illustrate the type of treatments are given above.

In the case of aortic dissection type A the false pipe includes the ascending part of aorta. The key issue is to press the separated membrane back to its original position and have it under support until it has healed and thereafter remove the stent. The stent device can as one alternative be inserted through the femoral arteries in the groins as an endovascular procedure. The femoral artery will thereby be punctured by a needle and a guiding wire will be inserted through the needle to the target area followed by an introducer in the groin. The stent will slide on the guide wire to the area of interest. The stent device is very compact during delivery. In the case of a self-expanding stent, it will in one preferred embodiment be firmly compressed and located inside a delivery sheath when introduced to the vasculature. The sliding on the guide wire located in a central channel of the device will be followed continuously with fluoroscopy and x-ray machines. The stent is detectable with x-ray, but preferably there are also in a preferred embodiment radioopaque markers on the delivery sheath which can be visually separated from the stent using x-ray. It will give the opportunity to step-wise follow the release of the stent from its delivery sheath. When the stent is in an ideal position, the delivery sheath will be retracted and the stent will expand to its predetermined size. This size is preferably adjusted to pre-procedural measurements of the aorta. These measurements can have their origins from diagnostic investigations based on undertakings like Computer Tomography (CT-scan), Magnetic resonance imaging (MRI), Nuclear Magnetic Resonance Imaging (NMRI), or Magnetic Resonance Tomography (MRT). In general the diameter of the stent should be considered to be somewhat oversized in comparison to the measured diameter of the aorta at the target area. This will secure its position and its action. In the case of aortic dissection type A the preferred diameter of the tubular body in its expanded state is 2.5 cm or above. The diameter can however be much larger, especially when the dissection is combined with a local dilatation in the treatment area, due to the formation of an aneurysm. In those latter cases diameters up to 10 cm might be required. However in the local treatment of dissections in the visceral arteries the diameters are preferably smaller than 2.5 cm and as low as 0.5 cm. The wall of the tubular body of the stent preferably has a radial and longitudinal strength to execute the wished action and to keep its position and shape. These mechanical properties will be achieved based on a balance between the thickness of the material used and the demand for degree of porosity dependent on the area of deployment. In areas in which the porosity needs to have a openings of diameter of 10 mm or more, a somewhat thicker thread might be needed to keep the mechanical properties. Thick in this situation is a diameter of the thread around 0.2 mm, when nitiniol as one preferred material is used as the memory alloy. Thin is a diameter of a nitinol thread around 0.025 mm. When using a thick thread, openings of 10 mm in diameter corresponds to a diameter 50 times greater than the diameter of the thread used. In areas where the deployment does not include crossing of side branches the material can be thinner and the walls might be denser, again thereby with kept mechanical properties. A more porous stent might also be preferable when flexibility is a key issue to adapt to a non-straight target independent of the presence of side branches. The thickness of the thread needed varies according to the mechanical properties of the material used. The length of the stent can vary a lot dependent on the extension of the dissection and its anatomical location. In general the whole dissection area can, but does not always need, a total coverage as long as the primary entry to the false lumen within the treated area. The length of the stent in a preferred embodiments is from approximately 1 cm in side branches to approximately 40 cm in the situation of coverage of the whole thoracic aorta.

After delivery of the stent the delivery sheath will be removed. The extension thread will in this situation slide inside the sheath. This thread can either have a length, where it is left inside the vasculature or on the skin surface in connection to the vascular access. In the case when the extension is left inside the vasculature, its end must be at a secure distance from the primary treatment area. In one preferred embodiment in which the ascending aorta is treated, the end should not be closer than the abdominal aorta. The reason is that the removal should preferably exclude mechanical manipulation in direct connection to the treated area. This area might still be sensitive to a sudden trauma after the initial healing, which would threaten the result. This is one of the advantages with the present invention to solutions represented in the prior art. In one of the preferred embodiments when the end of the thread is left on the skin surface in connection to the vascular access, the end is preferably secured with a waterproof and adhesive bandage that totally covers the end. The two positions have different pros and cons. If left inside the vasculature there is no risk of unplanned external manipulation and less risk for infection but an additional interventional procedure will be needed. If left on the skin surface in connection to the vascular access, there are minimal risks for external manipulation and infection but a very smooth removal without any need for extra instruments or additional interventions into the vasculature will be possible. This latter removal will be executed simply through pulling at the end of the extension left on the skin surface in connection to the previous vascular access. This pulling will release the reversible bind-off at the base of the tubular stent and the stent will start to disintegrate to the one single thread from which it was originally made. Alternatively the extension can have its end in the subcutaneous tissue, which will secure the involuntary pulling of the extension and reduce the risk of infection keeping the advantage of no additional devices or intravascular interventions at removal. In this situation a small incision in local anesthesia will be performed and then pulling of the extension by hand to reach total removal as one single thread.

The disintegration should preferably be continuously followed by fluoroscopy. As follow up and control of the final result CT-scan, MRI, NMRI, or MRT can be valid alternatives. In the case when the extension is left inside the vasculature, its end must be grabbed. The femoral artery as one preferred alternative will thereby be punctured again by a needle and a guiding wire can be inserted through the needle to the target area followed by an introducer in the groin. Alternatively the grabbing snare or something functionally alike, can be introduced without a guide wire. The snare will encircle the free end and pulled until the end is grabbed. The removal and control after completion will thereafter follow the same steps as described above. Alternatively the extension can have its end in the subcutaneous tissue, which will secure the involuntary pulling of the extension and reduce the risk of infection keeping the advantage of no additional devices or intravascular interventions at removal. In this latter situation a small incision in local anesthesia will be performed and then pulling of the extension by hand to reach total removal as one single thread.

The description of the procedure will follow the same principal steps when using shape memory polymers as alternative to self-expanding material.

The same principal steps as mentioned above will also be followed independent on the location of the vascular access. The same holds when using a material that is not self-expanding with the exception of the delivery. As previously described such a stent in a preferred embodiment is mounted on a deflated balloon, The balloon is connected to a shaft and the balloon, stent and partly the shaft are all located within the delivery sheath. The shaft extends beyond the delivery sheath and the introducer in the groin to be present externally and under direct control. The balloon and the stent are both firmly compressed in their positions when located inside the delivery sheath. After the retraction of the delivery sheath the balloon with its mounted stent will be hold in place by the external shaft and the position will be continuously controlled by fluoroscopy. The balloon will be inflated until the stent reaches its appropriate size with direct contact with the vascular wall. After deflating of the balloon the stent will remain in its planned location and the balloon will be retrieved. One advantage with not self-expanding materials is that some of them have greater mechanical strength. This is the case with one preferred embodiment using stainless steel. The result, according to the discussion above, is that the radial and longitudinal strength can be achieved by using thinner threads, resulting in a preferred increase in the ratio between diameter of the holes and the diameter of the thread used, thereby providing greater porosity. The gain in porosity is to a certain extent paid by a loss in flexibility. Obviously different materials will result in different characteristics of the end product. It is not excluded that a treatment area may have different demands in different parts. It is therefore within the range of possible treatments with the presented invention to use more than one stent in the same patient, combining stents with different characteristics. For a treatment with multiple stents either the same or different vascular accesses can be used.

The stent should preferably be removed after appropriate time, which time will vary dependent on location and length of the dissection. The length in time can vary from days, weeks to months.

The described removable stent used in the setting of vascular dissection has the same mechanical, back-bone material and design characteristics when used as a carrier for treatment of cancer in tubular systems. This is specially the case when the stent is delivered through the vascular system as described but used as therapy against parenchymal cancer. This is when the cancer cells do not have their origin in the vasculature but the route is used to treat an adjacent parenchymal cancer in organs like the lungs, liver and brain. Not only will the characteristics of the stent itself be the same but also its positioning and removal will follow the same principles. This statement is identical also when using the venous system to reach the target.

As discussed above, the described removable stent used in the setting of vascular dissection has the same mechanical, back-bone material and design characteristics when used as a carrier for treatment of cancer in tubular systems. In cancer in the gastro-intestinal tract including the esophagus or in the hepatico-pancreatico-biliary system or the pulmonary tract, as illustrated in FIG. 23, the methods to reach the targets and to remove the stent will be slightly different. Those minor differences have already been described in detail above or are obvious to a person skilled in the art.

Even if the stent used for cancer treatment has the same mechanical, back-bone material and design characteristics, it varies in its ability to carry a treatment. The treatment agents may be present through a coating that is a vehicle for drugs or irradiation agents. Alternatively that the backbone material is combined with drugs or radiation sources making a slow release compound, still ending up with a stent which has the same mechanical and design characteristics as described in detail above. The reason is that also in this modality the stent preferably exerts a pressure towards the cancer area to have an effect by applying the radiation or chemotherapy in direct contact to the cancer cells. Furthermore, the stent uses the same principles as described above to keep its position. In summary a very similar type of stent will be used for treatment of cancer, which only differs in the aspect that it beyond its mechanical properties delivers a biological impact on the surrounding tissue.

Such and other obvious modifications must be considered to be within the scope of the present invention, as it is defined by the appended claims. It should be noted that the abovementioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A removable stent comprising:
a porous tubular body formed by at least one continuous thread arranged in interconnected loops and including a reversible bind-off at one end of the tubular body, mechanically securing each loop at said end of the tubular body apart from a single releasable loop,
wherein the end of said tubular body including said reversible bind-off comprises a wale in which all loops are mechanically secured by said reversible bind-off, and wherein at least one mechanically secured intermediate loop is arranged between said wale and said single releasable loop.

2. The removable stent of claim 1, wherein the stent is expandable from a contracted insertion state to an expanded use state.

3. The removable stent of claim 1, wherein the at least one continuous thread extends with a loose end from said single releasable loop, thereby enabling release of said reversible bind-off by pulling said loose end, and unraveling of the interconnected loops by further pulling of the loose end.

4. The removable stent of claim 3, wherein said loose end has a length extension being larger than the axial length of the tubular body.

5. The removable stent of claim 4, wherein said loose end has a length extension being larger than two times the axial length of the tubular body.

6. The removable stent of claim 1, wherein the loops of the at least one continuous thread are interconnected by way of knitting.

7. The removable stent of claim 1, wherein an end of the tubular body being opposite to the end including the reversible bind-off comprises a mechanically secured cast-on.

8. The removable stent of claim 1, wherein the at least one continuous thread comprises a material having a shape memory.

9. The removable stent of claim 8, wherein the at least one continuous thread comprises a material including at least one of a memory alloy and a memory polymer.

10. The removable stent of claim 9, wherein the memory alloy is nitinol.

11. The removable stent of claim 1, wherein the at least one continuous thread comprises a material not having a shape memory.

12. The removable stent of claim 11, wherein the at least one continuous thread comprises at least one of stainless steel, carbon, and plastic material.

13. The removable stent of claim 1, wherein the tubular body includes a porosity in the range 0.73-1.

14. The removable stent of claim 1, wherein the tubular body has a sparsity in the range 0.05-0.6.

15. The removable stent of claim 1, further comprising a bioactive agent.

16. The removable stent of claim 1, further comprising a radioactive agent.

17. The removable stint of claim 1, wherein each mechanically secured loop of the wale is further looped over an adjacent stitch within the wale.

18. A method for producing a removable stent, the method comprising:
forming at least one continuous thread into interconnected loops, thereby forming a porous tubular body; and
providing a reversible bind-off at one end of the tubular body, mechanically securing each loop at said end of the tubular body apart from a single releasable loop,
wherein the end of said tubular body including said reversible bind-off comprises a wale in which all loops are mechanically secured by said reversible bind-off, and wherein at least one mechanically secured intermediate loop is arranged between said wale and said single releasable loop.

19. The method of claim 18, wherein the forming of at least one continuous thread into interconnected loops is made by knitting.

20. The method of claim 18, wherein the at least one continuous thread is of metal.

21. The method of claim 18, wherein the at least one continuous thread is further arranged to extend with a loose end from said single releasable loop, thereby enabling release of said reversible bind-off by pulling said loose end, and unraveling of the interconnected loops by further pulling of the loose end.

22. The method of claim 18, further comprising mechanically securing an end of the tubular body being opposite to the end having the reversible bind-off by way of a cast-on.

23. The method of claim 18, further comprising providing at least one of a bioactive agent and a radioactive agent on or in at least part of the at least one continuous thread.

24. The method of claim 18, wherein the at least one continuous thread includes a metal alloy.

\* \* \* \* \*